(12) United States Patent
Idogawa et al.

(10) Patent No.: US 8,686,127 B2
(45) Date of Patent: Apr. 1, 2014

(54) APOPTOSIS INDUCER

(75) Inventors: Masashi Idogawa, Sapporo (JP); Yasushi Sasaki, Sapporo (JP); Takashi Tokino, Sapporo (JP)

(73) Assignee: LSIP, LLC, Tokyo (JP)

( * ) Notice: Subject to any disclaimer, the term of this patent is extended or adjusted under 35 U.S.C. 154(b) by 0 days.

(21) Appl. No.: 12/937,107

(22) PCT Filed: Apr. 13, 2009

(86) PCT No.: PCT/JP2009/001701
§ 371 (c)(1),
(2), (4) Date: Dec. 22, 2010

(87) PCT Pub. No.: WO2009/125607
PCT Pub. Date: Oct. 15, 2009

(65) Prior Publication Data
US 2011/0105589 A1    May 5, 2011

Related U.S. Application Data

(60) Provisional application No. 61/044,061, filed on Apr. 11, 2008.

(51) Int. Cl.
C07H 21/04 (2006.01)

(52) U.S. Cl.
USPC ............... 536/24.5; 536/24.31; 536/24.1

(58) Field of Classification Search
None
See application file for complete search history.

(56) References Cited

U.S. PATENT DOCUMENTS

| | | | |
|---|---|---|---|
| 5,734,039 A * | 3/1998 | Calabretta et al. | 536/24.5 |
| 6,627,189 B1 | 9/2003 | Roth | |
| 2002/0086840 A1 | 7/2002 | Zarling | |
| 2005/0032728 A1* | 2/2005 | Gjerset et al. | 514/44 |
| 2006/0052322 A1* | 3/2006 | Roth et al. | 514/44 |
| 2007/0122385 A1 | 5/2007 | Carette | |

FOREIGN PATENT DOCUMENTS

| | | |
|---|---|---|
| JP | 2000-354488 A | 12/2000 |
| WO | 2005/042705 A2 | 5/2005 |
| WO | 2006/021894 A2 | 3/2006 |
| WO | 2006/116512 A1 | 11/2006 |
| WO | 2007/031091 A2 | 3/2007 |

OTHER PUBLICATIONS

Fan et al. (Mol. Cancer Ther 2003: vol. 2: 773-782).*
Zhu et al. (BMC Mol Biol 2007: 8:98, 1-11).*
European Search Report, Oct. 12, 2011.
Sato, Norihiro et al., Enhancement of drug-induced apoptosis by antisense oligodeoxynucleotides targeted against Mdm2 and p21WAF1/CIP1, Anticancer Research, vol. 20, No. 2A, Mar. 2000, pp. 837-842.
Chung, K. H. et al., Polycistronic RNA polymerase II expression vectors for RNA interference based on BIC/miR-155, Nucleic Acids Res, 2006, vol. 34, No. 7, p. e53.
Matsuhashi, N. et al., p53 depedence and apoptosis in response to FP treatment with p53-transfected colon cancer cell lines by use of thin layer collagen gel, Oncol Rep, 2004, vol. 12, No. 2, p. 357-61.
Broude, E. V. et al., p21 (CDKNIA) is a negative regulator of p53 stability, Cell Cycle, 2007, vol. 6, No. 12, 1468-71.
Giannakakou, P. et al., Low concentrations of paclitaxel induce cell type-dependent p53, p21 and G1/G2 arrest instead of mitotic arrest: moleculer determinants of paclitaxel-induced cytotoxicity, Oncogene, 2001, vol. 20, No. 29, p. 3806-13.
Mueller, S. et al., p21WAF1 regulates anchorage-independent growth of HCT116 colon carcinoma cells via E-cadherin expression, Cancer Res, 2000, vol. 60, No. 1, p. 156-63.
Arima, Y. et al., Transcriptional blockade induces p53-dependent apoptosis associated with translocation of p53 to mitochondria, J Biol Chem, 2005, vol. 280, No. 19, p. 19166-76.
Imai-Nishiyama, H. et al., Double knockdown of alpha1, 6-fucosyltransferase (FUT8) and GDP-mannose 4, 6-dehydratase (GMD) in antibody-producing cells: a new strategy for generating fully non-fucosylated therapeutic antibodies with enhanced ADCC, MBC Biotechnol, 2007, vol. 7, p. 84 (p. 1-13).
Namoto, M. et al., Heterogeneous induction of apoptosis in colon cancer cells by wild-type p53 gene transfection, Int J Oncol, 1998, vol. 12, No. 4, p. 777-84.
Essmann, F. et al., Irradiation-induced translocation of p53 to mitochondria in the absence of apoptosis, J Biol Chem, 2005, vol. 280, No. 44, p. 37169-77.
Sakamuro, D. et al., The polyproline region of p53 is required activate apoptosis but not growth arrest, Oncogene, 1997, vol. 15, No. 8, p. 887-98.
Chiang, C. T. et al., Sensitizing HER2-overexpressing cancer cells to luteolin-induced apoptosis througth suppressing p21 (WAF1/CIP1) expression with rapamycin, Mol Cancer Ther, 2007, vol. 6, No. 7, p. 2127-38.
Khong, T et al., Flavopiridol decreases the level of p21 and induces apoptosis in human myeloma cell lines, Blood, 2005, vol. 106, No. 11, p. 381B.
Hollstein et al, Sceince 1991;253:49-53.
Levine et al, Nature 1991;351:453-6.
Vogelstein et al, Nature 2000;408:307-10.
Clarke et al., Oncogene 1994;9:1767-73.
Merritt et al., Cancer Res 1994;54:614-7.
Poeta et al., N Engl J Med 2007;357:2552-61.
Patocs et al., N Engl J Med 2007;357:2543-51.
INGN 201: Ad-p53, Ad5CMV-p53, adenoviral p53, p53 gene therapy—introgen, RPR/INGN 201. Drugs R D 2007; 8:176-87.
Roth et al., Nat Med 1996; 2:985-91.
Swisher et al., J Natl Cancer Inst 1999; 91:763-71.

(Continued)

*Primary Examiner* — Kimberly Chong
(74) *Attorney, Agent, or Firm* — Hogan Lovells US LLP

(57) ABSTRACT

This invention relates to an agent, a composition and a product comprising at least one apoptosis-inducing substance, and at least one substance which inhibits expression and/or activity of an apoptosis-inhibiting substance; a method for inducing apoptosis or for treating a proliferative disease using one or more of them; a nucleic acid construct comprising a nucleic acid molecule encoding a protein to be expressed and a nucleic acid molecule which inhibits expression of an undesired protein; and a method for expressing a desired protein in a cell while inhibiting the expression of an undesired protein.

10 Claims, 16 Drawing Sheets

(56) References Cited

OTHER PUBLICATIONS

Nemunaitis et al., J Clin Oncol 2000; 18:609-22.
Riley et al., Nat Rev Mol Cell Biol 2008; 9:402-12.
Zhang et al., Environ Health Perspect 2007; 115:653-8.
el-Deiry et al., Cell 1993; 75:817-25.
Dulic et al., Cell 1994; 76:1013-23.
Deng et al., Cell 1995; 82:675-84.
Brugarolas et al., Nature 1995; 377:552-7.
Chan et al., Genes Dev 2000; 14:1584-8.
Waldman et al., Nat Med 1997; 3:1034-6.
Waldman et al., Nature 1996; 381:713-6.
Van Nguyen et al., J Exp Med 2007; 204:1453-61.
Poole et al., Oncogene 2004; 23:8128-34.
Martin-Caballero et al., Cancer Res 2001; 61:6234-8.
Barboza et al., Proc Natl Acad Sci U S A 2006; 103:19842-7.
Topley et al., Proc Natl Acad Sci U S A 1999; 96:9089-94.
Philipp et al., Oncogene 1999; 18:4689-98.
Jackson et al., Cancer Res 2003; 63:3021-5.
van de Wetering et al., Cell 2002; 111:241-50.
Gartel et al., Cancer Res 2005; 65:3980-5.
Stiewe, Nat Rev Cancer. 2007;7(3):165-8.
Hannon et al., Nature 2002; 418:244-51.
Rana et al., Nat Rev Mol Cell Biol 2007; 8:23-36.
Brummelkamp et al., Science 2002; 296:550-3.
Paddison et al., Genes Dev 2002; 16:948-58.
Paul et al., Nat Biotechnol 2002; 20:505-8.
Ambros et al., Nature 2004; 431:350-5.
Ambros et al., Cell 2001; 107:823-6.
Sasaki et al., Mol Cancer Ther 2008; 7:779-87.
Yamato, K., et al., Induction of cell death in human papillomavirus 18-positive cervical cancer cells by E6 siRNA, Cancer Gene Therapy, 2006, 13, 234-241.
Sima, N., et al., Antisense targeting to human papillomavirus 18 E6/E7 affects the proliferation and apoptosis of human cervical carcinoma: an in vitro experiment with HeLa cells, Zhonghua Yi Xue Za Zhi, 2007, 87(23), 1618-1621. [English Abstract].
Wang, P., et al., Effect of small interference RNA on E6, E7 mRNA of human papillomavirus type-18 in cervical cancer cells, Zhonghua Fu Chan Ke Za Zhi, 2006, 41(3), 190-193. [English Abstract].
Ambrosini, G., et al., The Cyclin-Dependent Kinase Inhibitor Flavopiridol Potentiates the Effects of Topoisomerase I Poisons by Suppressing Rad51 Expression in a p53-Dependent Manner, Cancer Res., 2008, 68(7), 2312-2320.

\* cited by examiner

Fig. 1
miR-p21A
[SEQ ID NO:20]
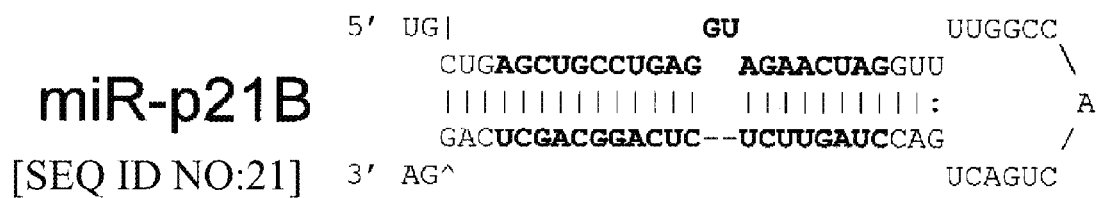
miR-p21B
[SEQ ID NO:21]
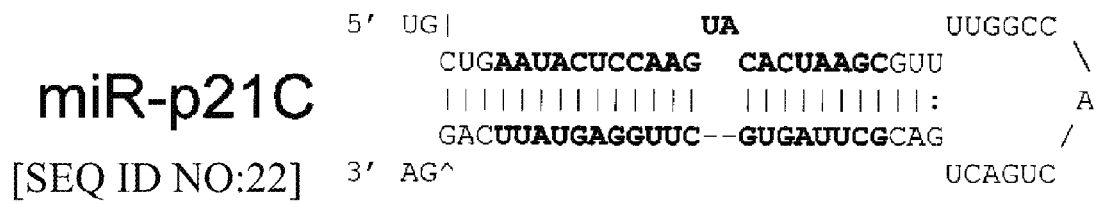
miR-p21C
[SEQ ID NO:22]

Fig. 12
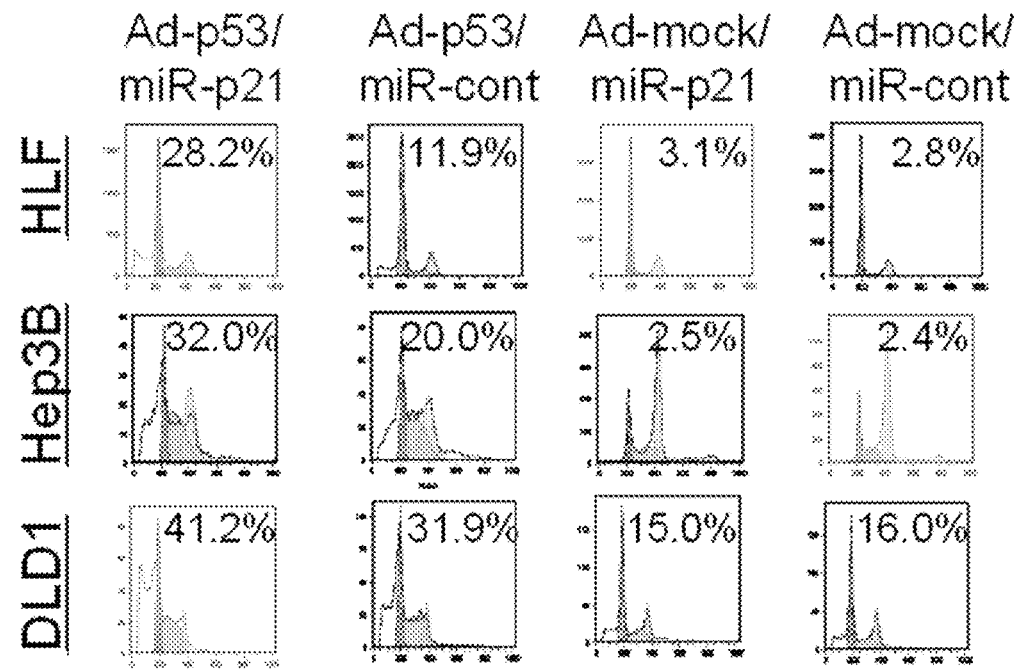
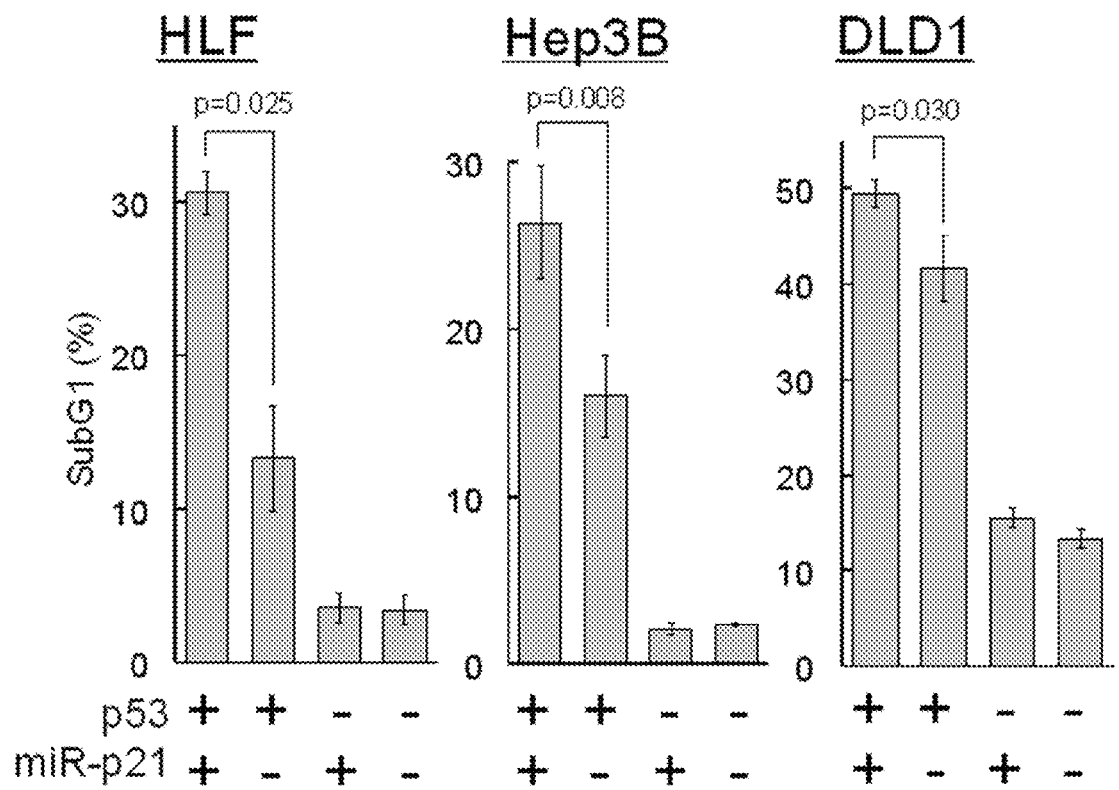

Fig. 16
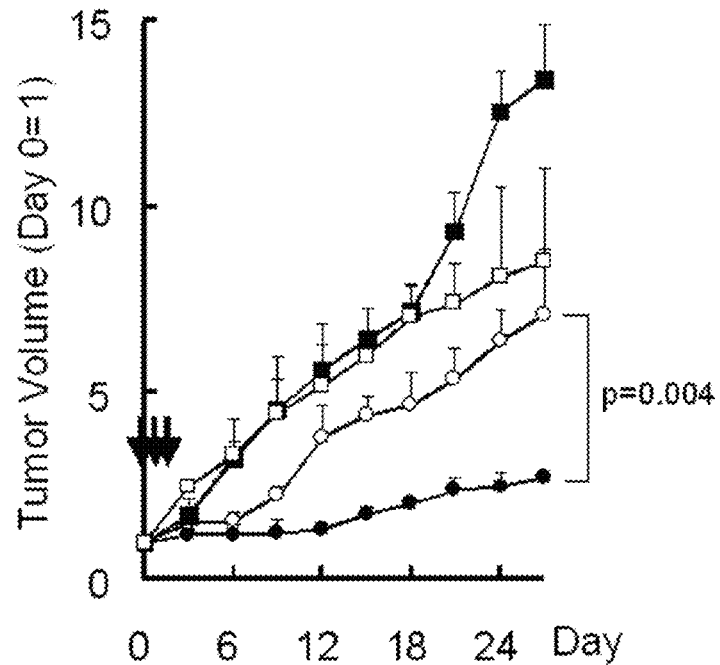
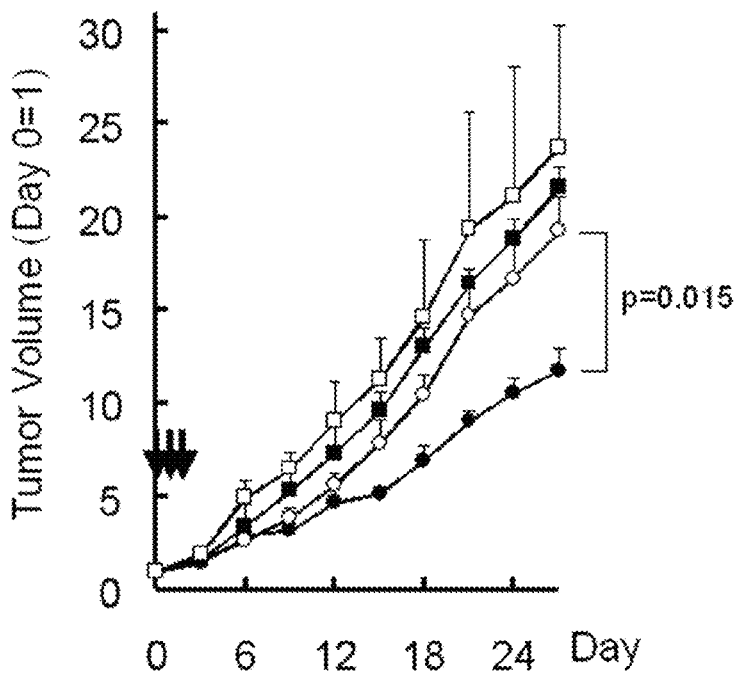

APOPTOSIS INDUCER

CROSS-REFERENCE TO RELATED APPLICATIONS

This application is the U.S. National Phase under 35 U.S.C. §371 of International Application PCT Patent Application No. PCT/JP2009/001701, filed on Apr. 13, 2009, which claims benefit of U.S. Provisional Patent Application Ser. No. 61/044,061, filed Apr. 11, 2008, the contents of which are hereby incorporated herein by reference in its entirety.

TECHNICAL FIELD

The present invention relates to an agent, a composition and a product for inducing apoptosis; a method for inducing apoptosis or for treating a proliferative disease using the agent, composition or product; a nucleic acid construct comprising a nucleic acid molecule encoding a protein to be expressed and a nucleic acid molecule which inhibits expression of an undesired protein; and a method for expressing a desired protein in a cell while inhibiting the expression of an undesired protein.

BACKGROUND ART p53 is one of the most important tumor suppressor genes. In approximately half of all human cancers, p53 is inactivated as a direct result of mutations in the p53 gene (Hollstein et al., Science 1991; 253:49-53, Levine et al., Nature 1991; 351:453-6). In other cancers, p53 is inactivated through its association with viral oncoproteins, or as a result of alterations in genes that are involved in the p53 signaling network (Vogelstein et al., Nature 2000; 408:307-10). Furthermore, mutation or deletion of p53 is related to poor prognosis and resistance to chemotherapy and radiation (Clarke et al., Oncogene 1994; 9:1767-73, Merritt et al., Cancer Res 1994; 54:614-7, Poeta et al., N Engl J Med 2007; 357:2552-61, Patocs et al., N Engl J Med 2007; 357:2543-51).

Vector-mediated gene transfer of p53 is viewed as a potentially effective cancer therapy. In fact, clinical trials of adenovirus-mediated p53 gene therapy are ongoing in patients with head and neck (Phase III), non-small cell lung (Phase II), breast (Phase II) and esophageal (Phase II) cancer (INGN 201: Ad-p53, Ad5CMV-p53, adenoviral p53, p53 gene therapy-introgen, RPR/INGN 201. Drugs R D 2007; 8:176-87). However, gene transfer of p53 does not always have a good therapeutic outcome for all cancers (Roth et al., Nat Med 1996; 2:985-91, Swisher et al., J Natl Cancer Inst 1999; 91:763-71, Nemunaitis et al., J Clin Oncol 2000; 18:609-22). Thus, further refinement in p53-directed gene therapy is required.

The activation of p53 is induced by a variety of cell stresses, such as DNA damage, oncogene activation, spindle damage and hypoxia. Activated p53 transactivates a number of genes, many of which are involved in DNA repair, cell cycle arrest and apoptosis (Riley et al., Nat Rev Mol Cell Biol 2008; 9:402-12). Depending on the cell type and intensity of stress, p53 activation induces either cell cycle arrest or apoptosis (Zhang et al., Environ Health Perspect 2007; 115:653-8). However, the precise mechanism that regulates whether a cell undergoes cell cycle arrest or apoptosis is still unclear.

SUMMARY OF INVENTION

Technical Problem

It is an object of the invention to provide a product that assures a good therapeutic outcome even in cancers that are resistant to a conventional gene transfer of p53.

Solution to Problem

It has now been shown that the outcome of p53-directed gene therapy is significantly improved by simultaneous inhibition of the expression of a p53-targeted gene involved in cell cycle arrest such as p21 (el-Deiry et al., Cell 1993; 75:817-25, Dulic et al., Cell 1994; 76:1013-23, Deng et al., Cell 1995; 82:675-84, Brugarolas et al., Nature 1995; 377:552-7). It was known that genes involved in cell cycle arrest work towards restoring genomic integrity by functioning in an anti-apoptotic manner (Chan et al., Genes Dev 2000; 14:1584-8, Waldman et al., Nat Med 1997; 3:1034-6, Waldman et al., Nature 1996; 381:713-6). On the other hand, there is evidence that such a gene also inhibits cell growth, which leads to tumor-suppression. Indeed, tumor susceptibility is increased in p21-null mice (Van Nguyen et al., J Exp Med 2007; 204:1453-61, Poole et al., Oncogene 2004; 23:8128-34, Martin-Caballero et al., Cancer Res 2001; 61:6234-8, Barboza et al., Proc Natl Acad Sci USA 2006; 103:19842-7), and mice that lack p21 are more prone to developing malignant skin tumors following exposure to carcinogens (Topley et al., Proc Natl Acad Sci USA 1999; 96:9089-94, Philipp et al., Oncogene 1999; 18:4689-98).

Following a single dose of gamma-irradiation, p21-deficient mice develop more tumors, and the tumors have an increased metastatic potential (Jackson et al., Cancer Res 2003; 63:3021-5). In addition, it has been shown that the suppression of p21 induces cell cycle progression, resulting in increased cell proliferation (van de Wetering et al., Cell 2002; 111:241-50, Gartel et al., Cancer Res 2005; 65:3980-5). Thus, the suppression of p21 was thought to increase the risk of tumor progression. Taken together, the effect of inhibition of a gene involved in cell cycle arrest on the outcome of p53-directed gene therapy was unpredictable. Therefore, the present finding showing that the inhibition of cell-cycle arrest gene enhances p53-induced tumor suppression is surprising.

Accordingly, in one aspect, the present invention provides an agent, a composition or a product comprising at least one apoptosis-inducing substance, and at least one substance which inhibits expression and/or activity of an apoptosis-inhibiting substance.

In one embodiment, the apoptosis-inducing substance is an apoptosis-inducing protein and/or nucleic acid molecule encoding the same.

In one embodiment, the apoptosis-inducing protein is a protein of a p53 family.

In one embodiment, the apoptosis-inhibiting substance is induced by the apoptosis-inducing substance.

In one embodiment, the apoptosis-inhibiting substance is selected from the group consisting of a protein involved in cell cycle arrest, an ubiquitin ligase and a dominant negative variant of a p53 family protein.

In one embodiment, the protein involved in cell cycle arrest is selected from the group consisting of p21, SFN, Gadd45 and p300.

In one embodiment, the ubiquitin ligase is MDM2.

In one embodiment, the substance which inhibits expression and/or activity of an apoptosis-inhibiting substance is a nucleic acid molecule which inhibits the expression of the apoptosis-inhibiting substance or a nucleic acid encoding the same.

In one embodiment, the nucleic acid molecule which inhibits the expression of the apoptosis-inhibiting substance is selected from the group consisting of antisense nucleic acid, ribozyme, aptamer and RNAi effector.

In one embodiment, the apoptosis-inducing protein and/or nucleic acid molecule encoding the same, and the substance which inhibits expression and/or activity of an apoptosis-inhibiting substance are present as a single substance.

In one embodiment, the agent, composition or product is formed as a single vector or a single nucleic acid construct containing a nucleic acid molecule encoding the apoptosis-inducing protein and a nucleic acid molecule which inhibits the expression of the apoptosis-inhibiting substance.

In one embodiment, the nucleic acid molecule encoding the apoptosis-inducing protein and the nucleic acid molecule which inhibits the expression of the apoptosis-inhibiting substance are operably linked to a same regulatory sequence such as promoter(s) and enhancer(s).

In one embodiment, the nucleic acid molecule encoding the apoptosis-inducing protein and the nucleic acid molecule which inhibits the expression of the apoptosis-inhibiting substance are expressed as a single primary transcript.

In one embodiment, the nucleic acid molecule encoding the apoptosis-inducing protein and the nucleic acid molecule which inhibits the expression of the apoptosis-inhibiting substance are expressed co-cistronically.

In another embodiment, the apoptosis-inducing protein and/or nucleic acid molecule encoding the same, and the substance which inhibits expression and/or activity of an apoptosis-inhibiting substance are present as separate substances.

In one embodiment, the agent, composition or product is for treating proliferative disease.

In one embodiment, the proliferative disease is selected from the group consisting of benign or malignant tumor, hyperplasia, keloid, Cushing syndrome, primary aldosteronism, erythroplakia, polycythemia vera, leukoplakia, hyperplastic scar, lichen planus and lentiginosis.

In another aspect, the present invention provides a method for inducing apoptosis of a cell comprising:
(a) providing the above-mentioned agent, composition or product, and
(b) introducing said agent, composition or product in the cell.

In one embodiment, the agent, composition or product is selected from the group consisting of a vector bearing a nucleic acid molecule encoding an apoptosis-inducing protein and a nucleic acid molecule which inhibits expression and/or activity of an apoptosis-inhibiting substance, or a set of vectors consisting of a vector bearing a nucleic acid molecule encoding an apoptosis-inducing protein and a vector bearing a nucleic acid molecule which inhibits expression and/or activity of an apoptosis-inhibiting substance.

In another aspect, the present invention provides a nucleic acid construct comprising:
a nucleic acid molecule encoding a protein to be expressed, and
a nucleic acid molecule which inhibits expression of an undesired protein.

In one embodiment, the protein to be expressed is an apoptosis-inducing protein.

In one embodiment, the apoptosis-inducing protein is a protein of a p53 family.

In one embodiment, the undesired protein is an apoptosis-inhibiting protein.

In one embodiment, the apoptosis-inhibiting protein is selected from the group consisting of a protein involved in cell cycle arrest, an ubiquitin ligase and a dominant negative variant of a p53 family protein.

In one embodiment, the nucleic acid molecule encoding a protein to be expressed and the nucleic acid molecule which inhibits expression of an undesired protein are operably linked to a same regulatory sequence such as promoter(s) and enhancer(s).

In one embodiment, the nucleic acid molecule encoding a protein to be expressed and the nucleic acid molecule which inhibits expression of an undesired protein are expressed as a single primary transcript.

In one embodiment, the nucleic acid molecule encoding a protein to be expressed and the nucleic acid molecule which inhibits expression of an undesired protein are expressed co-cistronically.

In another aspect, the present invention provides a vector comprising the above-mentioned nucleic acid construct.

In another aspect, the present invention provides a method for expressing a desired protein in a cell while inhibiting the expression of an undesired protein, comprising:
(a) providing the above-mentioned nucleic acid construct and/or vector, and
(b) introducing the nucleic acid construct and/or vector in the cell.

Advantageous Effects of Invention

By using the agent, composition, product or the method of the present invention, it is possible to induce apoptosis in cells, such as tumor cells, that are resistant to a treatment by an apoptosis-inducing protein alone, such that a great contribution to medical and veterinary fields can be expected. Furthermore, the nucleic acid construct or vector of the present invention makes it possible to express a desired protein in a cell while inhibiting the expression of an undesired protein, which may be useful for many applications, in particular in those cases that the undesired protein is induced by the expression of the desired protein.

BRIEF DESCRIPTION OF DRAWINGS

FIG. 1 shows the folded structure of three different p21-specific pre-miRNAs, miR-p21A [SEQ ID NO:20], B [SEQ ID NO:21] and C [SEQ ID NO:22]. The double-stranded RNA corresponding to human p21 targeting sequences are shown in bold (miR-p21A: 5' AUAGGGUGCCCU-UC-UU-CUUGUG 3' [SEQ ID NO:23], 3' AUCCCACGGGA--AA-GAACAC 5' [SEQ ID NO:24]; miR-p21B: 5' AGCUGC-CUGAG-GU-AGAACUAG 3' [SEQ ID NO:25], 3' UCGACGGACUC--UCUUGAU 5' [SEQ ID NO:26]; miR-p21A: 5' AAUACUCCAAG-UA-CACUAAGC 3' [SEQ ID NO:27], 3' UUAUGAGGUUC--GUGAUUCG 5' [SEQ ID NO:28]).

Figure 4:
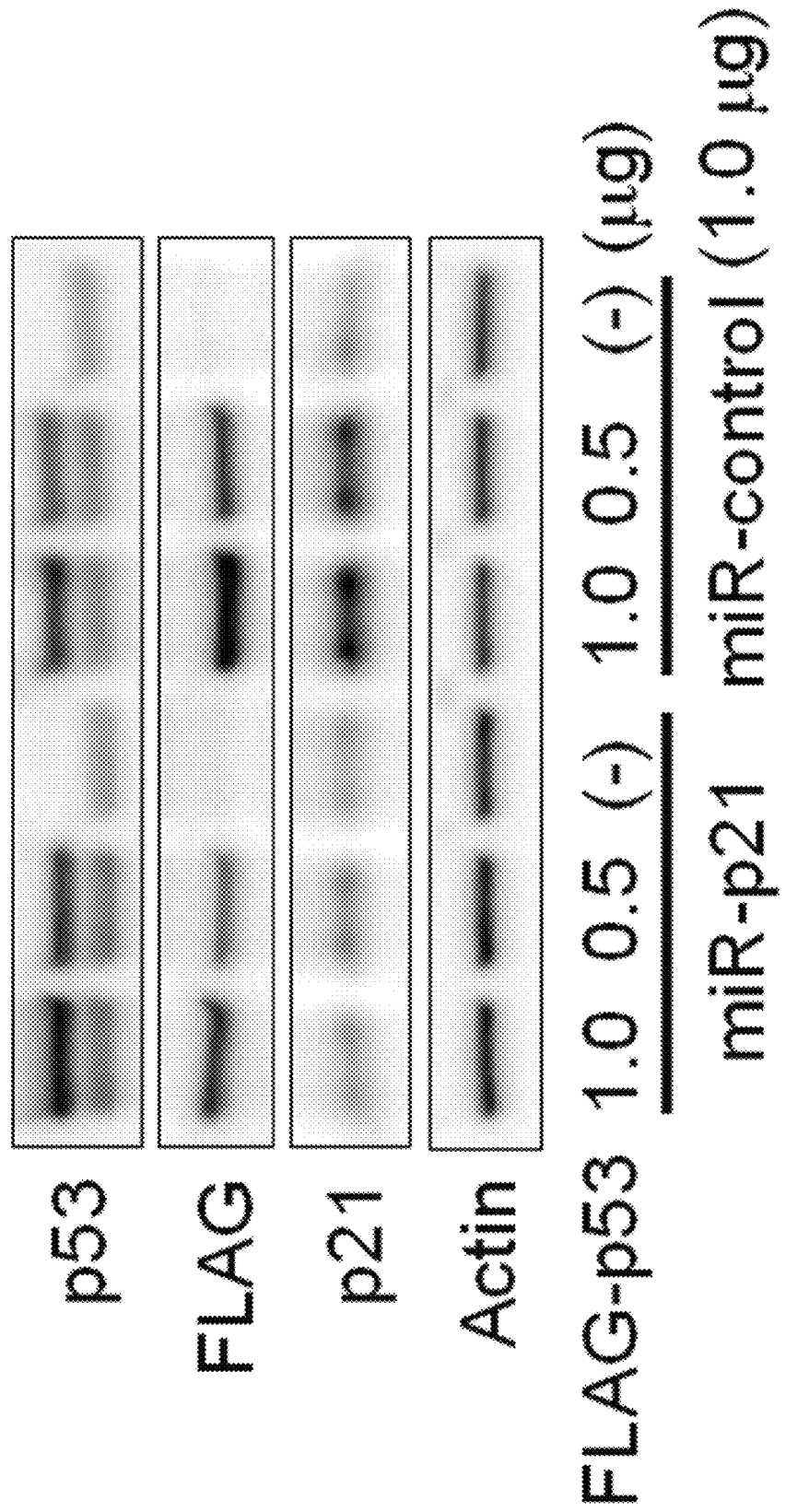

FIG. 4 shows the suppression of p21 expression by artificial miRNAs in cells treated by a p53 expression vector. HEK293 cells were co-transfected with the indicated amounts of pCMV-Tag2-FLAG-p53 (FLAG-p53), and either pcDNA6.2-miR-p21, which encodes a tandem array of miR-p21A, B and C (miR-p21), or a control vector (miR-control). Total cell lysate was analyzed 24 hrs. after transfection by Western blot using anti-p53, -FLAG, -p21 and -actin antibodies.

Figure 5:
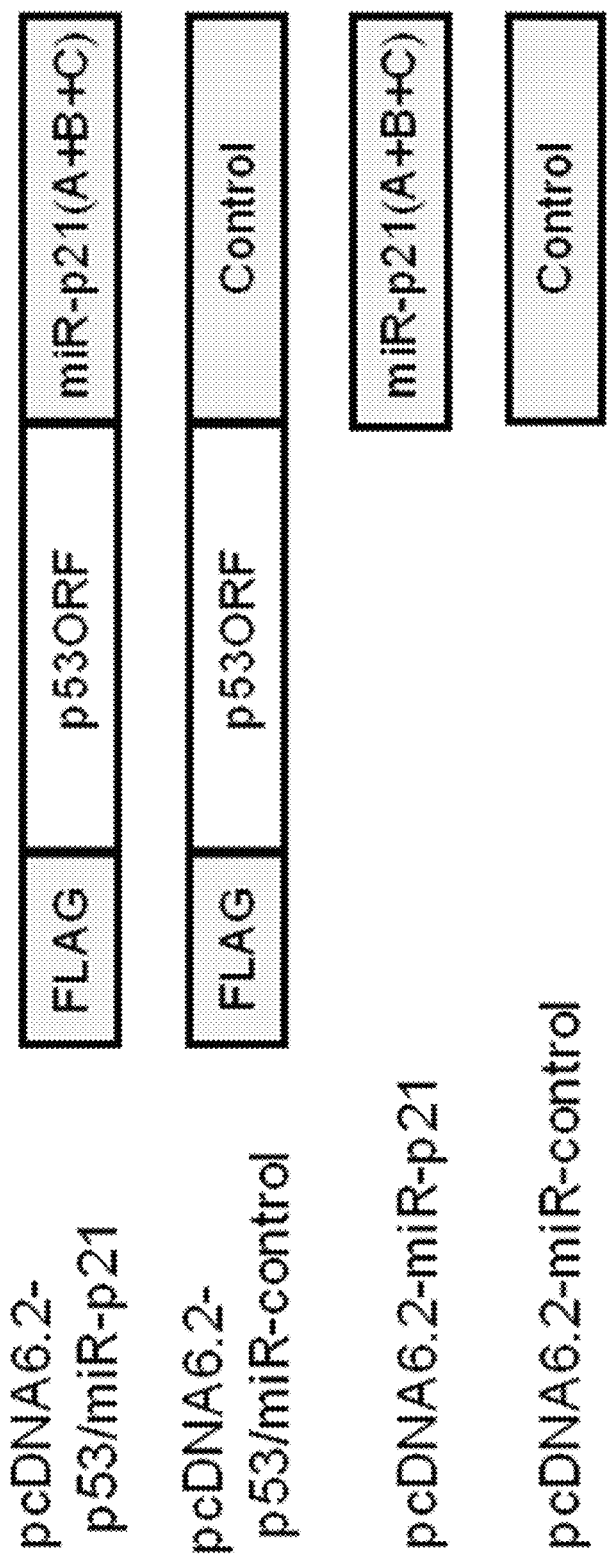

FIG. 5 is a schematic representation of the plasmid vectors used in the present Examples. Vectors were generated from the parental plasmid pcDNA6.2-GW/miR. The p53 ORF, which included sequences for the FLAG epitope, was inserted at the 5' side of the cluster of multiple miRNAs. Thus, pcDNA6.2-p53/miR-p21, for example, enables co-cistronic expression of the FLAG-tagged p53 protein and three different p21-specific miRNAs in one primary transcript under the control of the CMV promoter.

Figure 6:
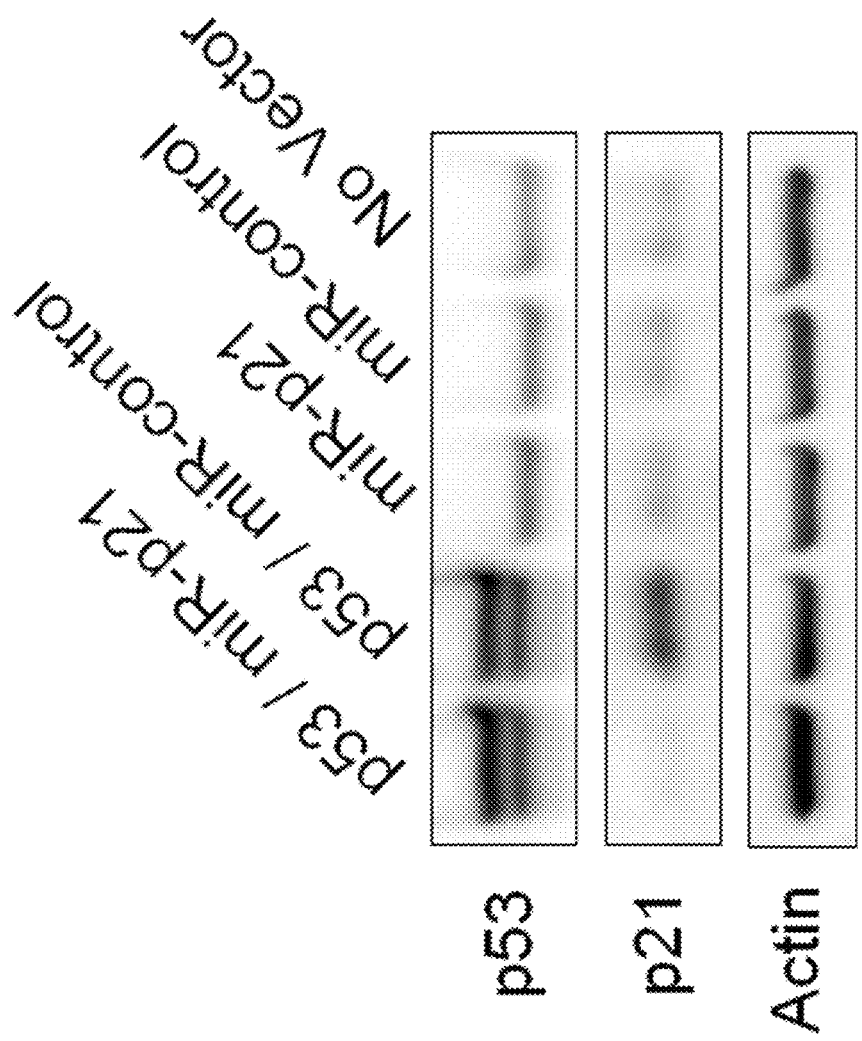

FIG. 6 shows the expression of p53 and suppression of p21 induction using a single plasmid vector. HEK293 cells were transfected with the indicated vectors (vectors as described in FIG. 5). Total cell lysate was analyzed 24 hrs. after transfection by Western blot using anti-p53, -p21 and -actin antibodies.

Figure 7:
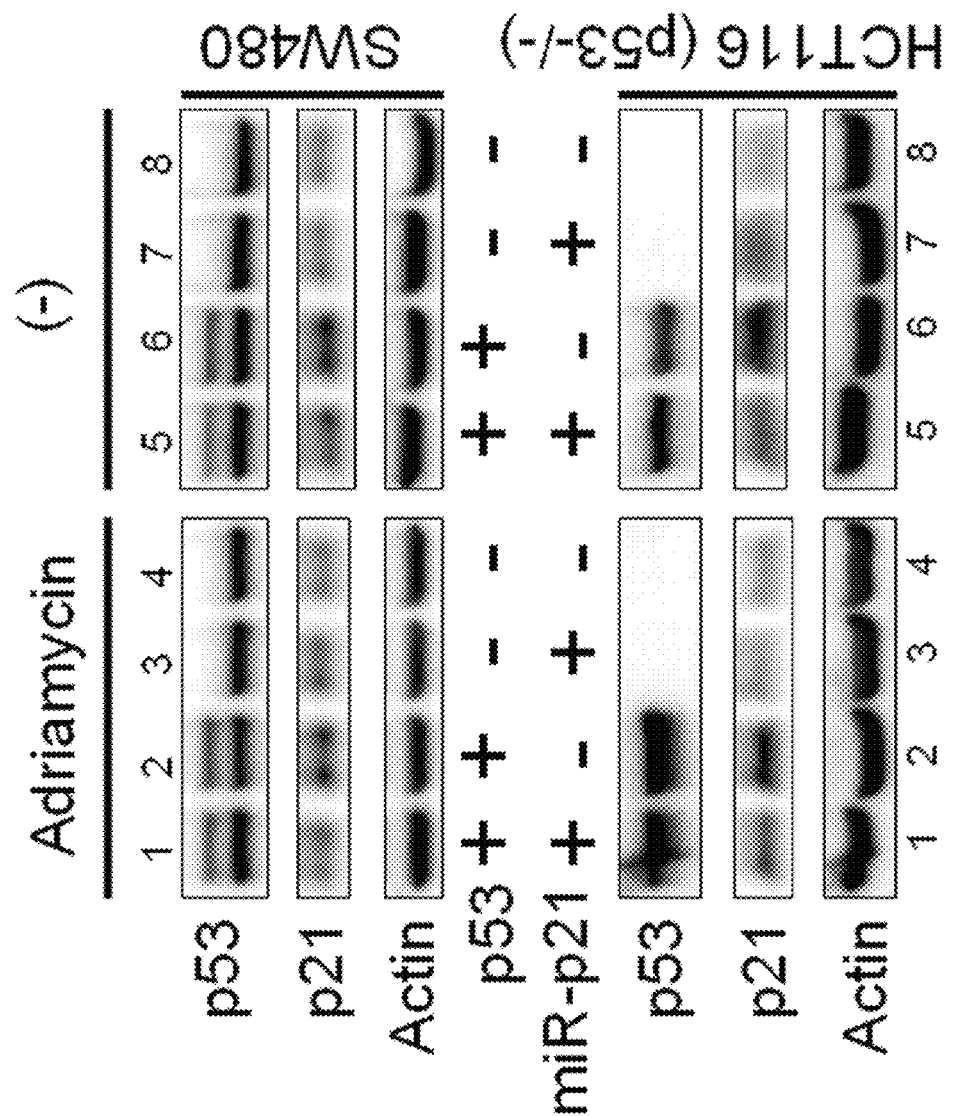

FIG. 7 shows the expression of p53 and suppression of p21 induction in cells treated by adriamycin using a single plasmid vector. SW480 and p53(−/−) HCT116 cells were transfected with the indicated vectors (lanes 1 and 5, pcDNA6.2-p53/miR-p21; lanes 2 and 6, pcDNA6.2-p53/miR-control; lanes 3 and 7, pcDNA6.2-miR-p21; lanes 4 and 8, pcDNA6.2-miR-control). (+) and (−) indicate the presence and absence of p53 and miR-p21 expression, respectively. After 24 hrs., the media was replaced with fresh media with (lanes 1 to 4) or without 0.5 microgram/ml of adriamycin (lanes 5 to 8), and the cells were allowed to incubate for an additional 24 hrs. Total cell lysate was analyzed by Western blot using anti-p53, -p21 and -actin antibodies.

Figure 8:
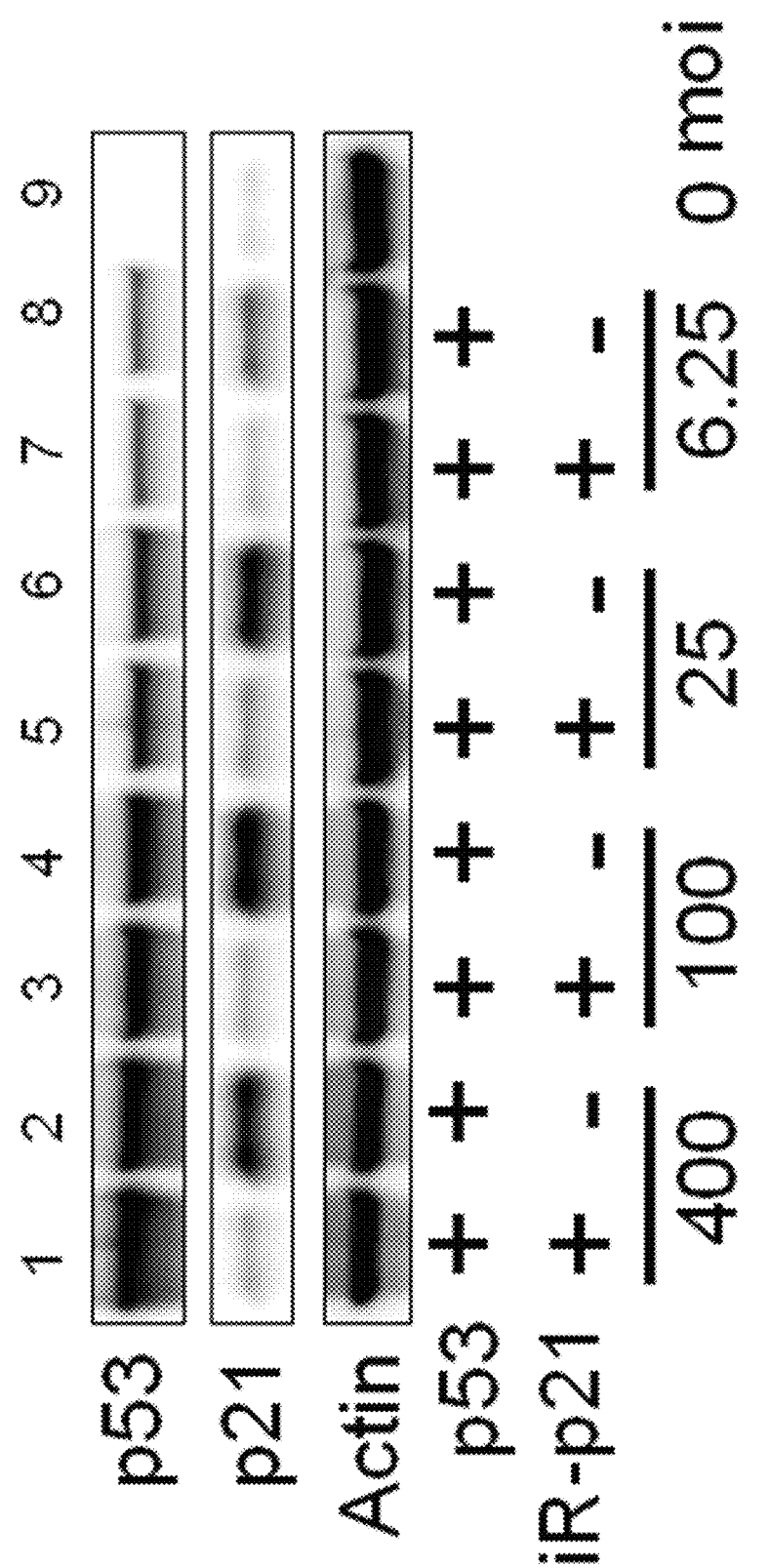

FIG. 8 shows the expression of p53 and suppression of p21 induction in cells treated by different doses of a recombinant adenovirus expressing p53 together with p21-specific miRNAs. p53(−/−) HCT116 cells were infected with Ad-p53/miR-p21 (lanes 1, 3, 5 and 7) or Ad-p53/miR-control (lanes 2, 4, 6 and 8) at the indicated moi. Total cell lysate was analyzed 24 hrs. after infection by Western blot using anti-p53, -p21 and -actin antibodies.

Figure 9:
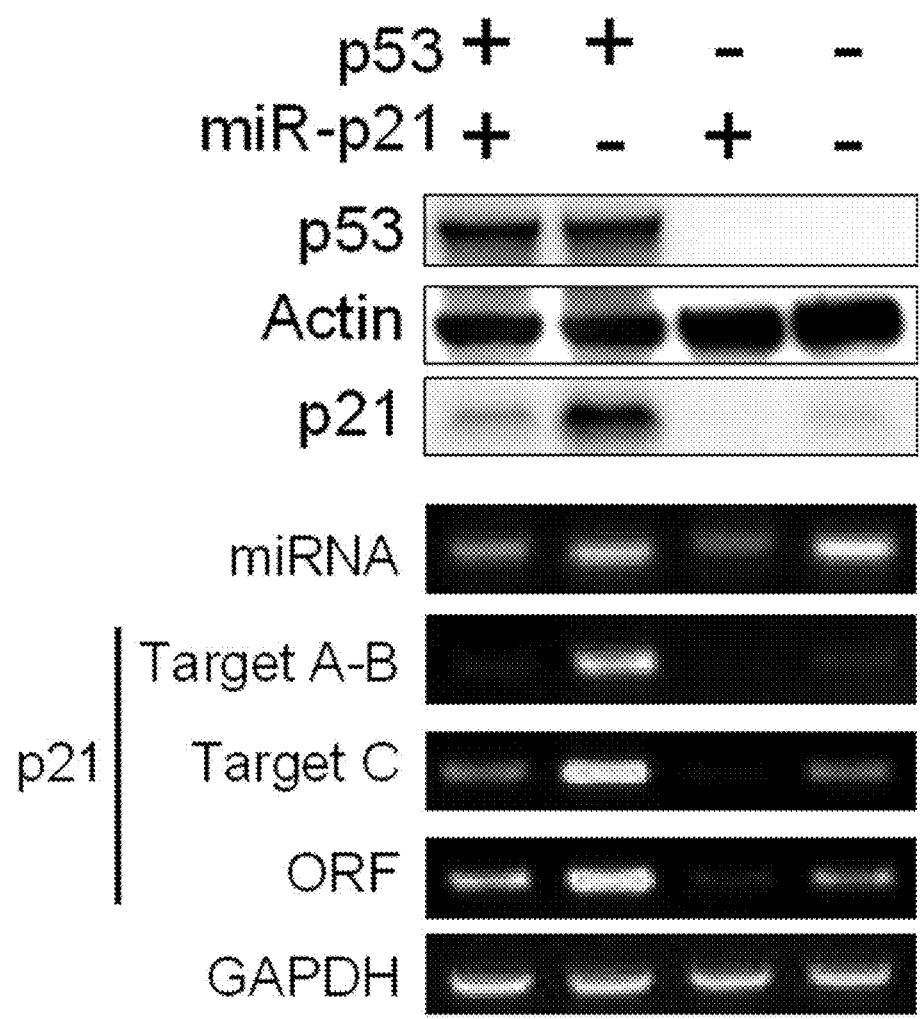

FIG. 9 shows the expression of p53 and suppression of p21 induction in cells treated by a recombinant adenovirus expressing p53 together with p21-specific miRNAs (upper 3 lines), as well as the expression of indicated mRNA (lower 5 lines). p53 (−/−) HCT116 cell was infected with the indicated recombinant adenoviruses at an moi of 100. Total cell lysate was analyzed 48 hrs. after infection by Western blot using anti-p53, -actin and -p21 antibodies. mRNA expression of vector-derived miRNA, p21 and GAPDH was also analyzed by RT-PCR. Target A-B: including the target site of miR-p21A and B (1327-1493). Target C: including the target site of miR-p21C (1525-1677). ORF: including ORF (523-778). The position numbers are based on the mRNA sequence of p21 (GenBank accession No.: NM_000389).

Figure 10:
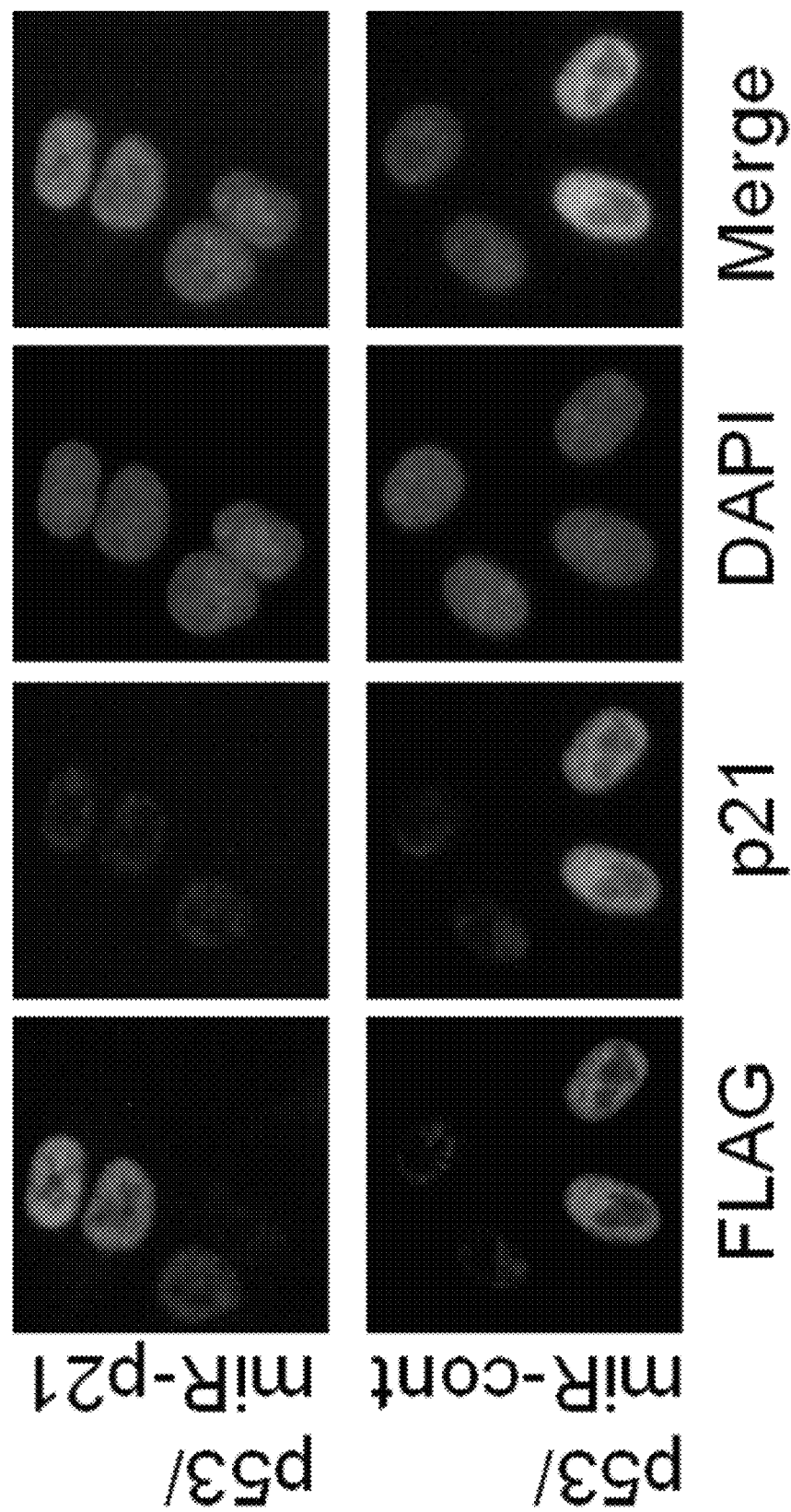

FIG. 10 shows the suppression of p21 induction in cells treated by a recombinant adenovirus expressing p53 together with p21-specific miRNAs. p53(−/−) HCT116 cells were infected with Ad-p53/miR-p21 or Ad-p53/miR-control at an moi of 100. Immunofluorescence staining was performed 24 hrs. after infection using anti-FLAG rabbit polyclonal antibody (red), anti-p21 mouse monoclonal antibody (green) and 4',6-diamidino-2-phenylindole (DAPI, blue).

Figure 11:
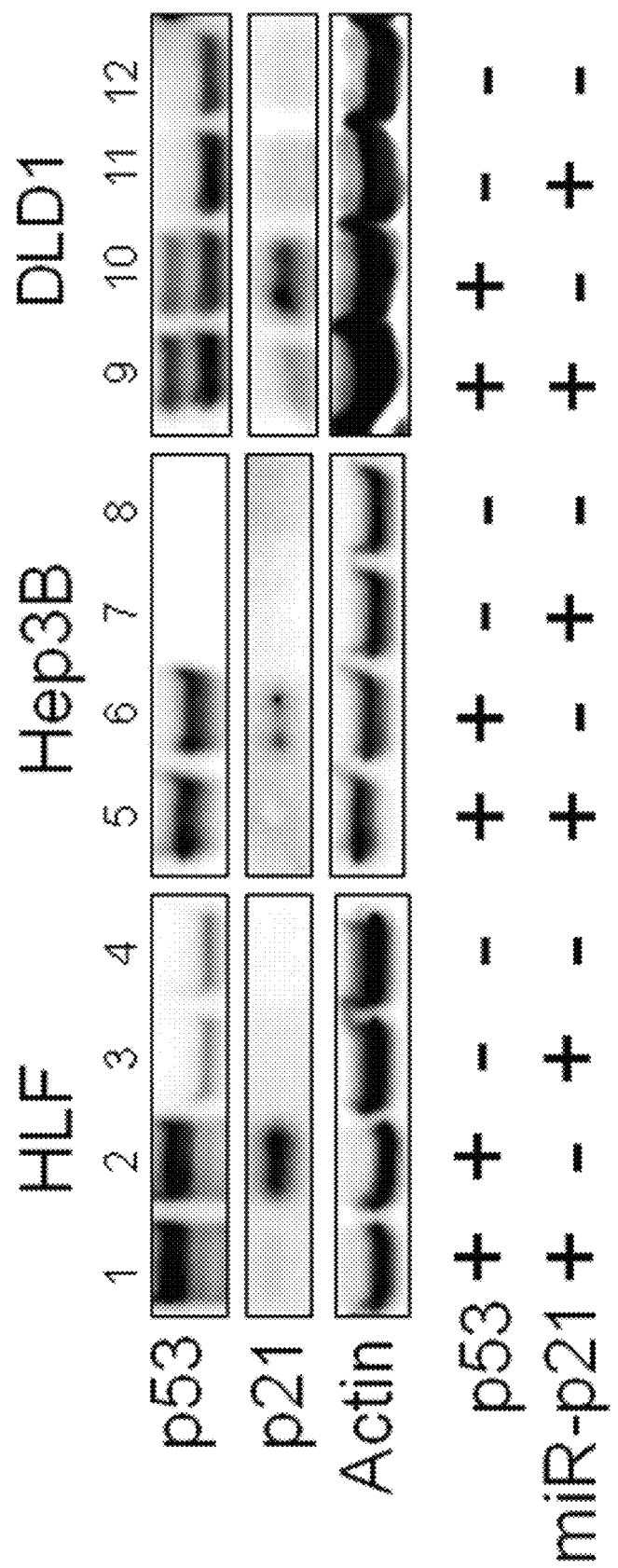

FIG. 11 shows the expression of p53 and the suppression of p21 induction in various cells treated by a recombinant adenovirus expressing p53 together with p21-specific miRNAs. HLF, Hep3B and DLD1 cells were infected with the indicated recombinant adenoviruses at an moi of 200 (lanes 1, 5 and 9: Ad-p53/miR-p21; lanes 2, 6 and 10: Ad-p53/miR-control; lanes 3, 7 and 11: Ad-mock/miR-p21; lanes 4, 8 and 12: Ad-mock/miR-control). Total cell lysate was analyzed 24 hrs. after infection by Western blot using anti-p53, -p21 and -actin antibodies.

FIG. 12 shows the proportion of cells undergoing apoptosis among various cells treated by a recombinant adenovirus expressing p53 together with p21-specific miRNAs. HLF, Hep3B and DLD1 cells were infected with the indicated recombinant adenoviruses, and then analyzed 48 hrs. after infection by flow cytometry. The percentage of cells in sub-G1 is indicated (top). The average of three independent experiments is also indicated (bottom). Error bars indicate S.E., and p-values were calculated by Student's t testing.

Figure 13:
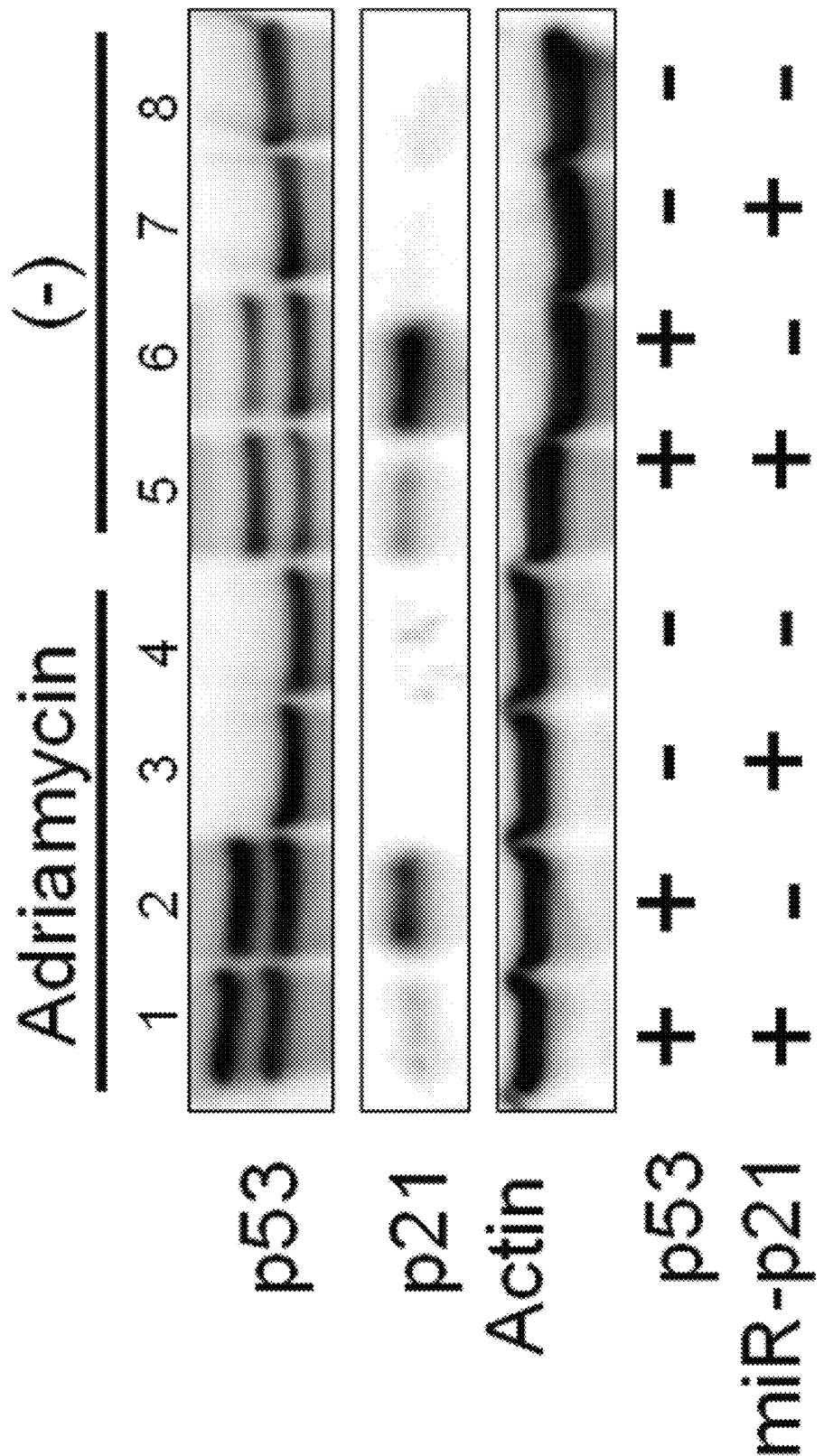

FIG. 13 shows the expression of p53 and the suppression of p21 induction cells treated by a recombinant adenovirus expressing p53 together with p21-specific miRNAs. SW480 cells were infected with the indicated adenoviruses at an moi of 200 (lanes 1 and 5: Ad-p53/miR-p21; lanes 2 and 6: Ad-p53/miR-control; lanes 3 and 7: Ad-mock/miR-p21; lanes 4 and 8: Ad-mock/miR-control). After 24 hrs., the media was replaced with fresh media with (lanes 1 to 4) or without 0.5 microgram/ml of adriamycin (lanes 5 to 8) and the cells were allowed to incubate for an additional 24 h. Total cell lysate was analyzed by Western blot using anti-p53, -p21 and -actin antibodies.

Figure 14:
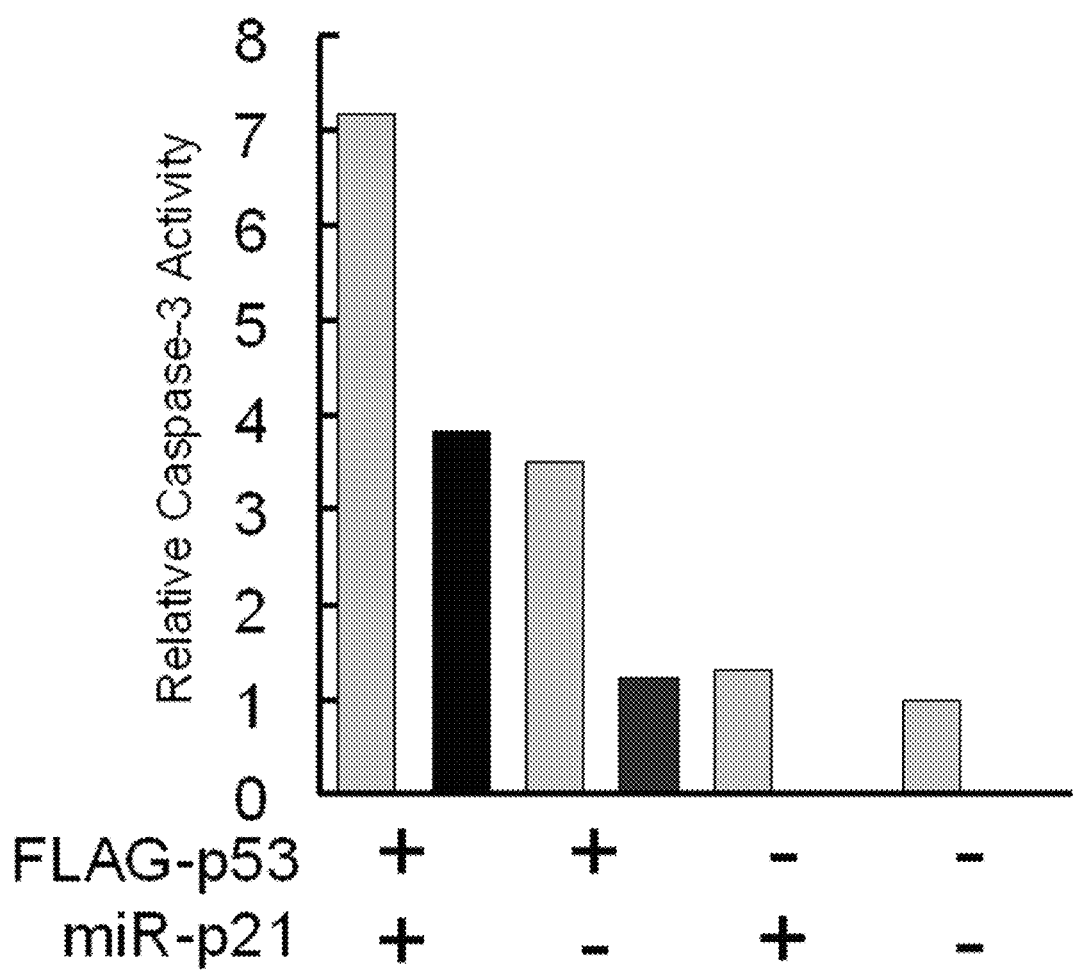

FIG. 14 shows the caspase-3 activity in cells treated by a recombinant adenovirus expressing p53 together with p21-specific miRNAs. Caspase-3 activity was assayed 72 hrs. after adenovirus infection. Cells treated with and without adriamycin are indicated by gray and black bars, respectively. Caspase-3 activity was normalized to Ad-mock/miR-control-infected cells treated with adriamycin.

Figure 15:
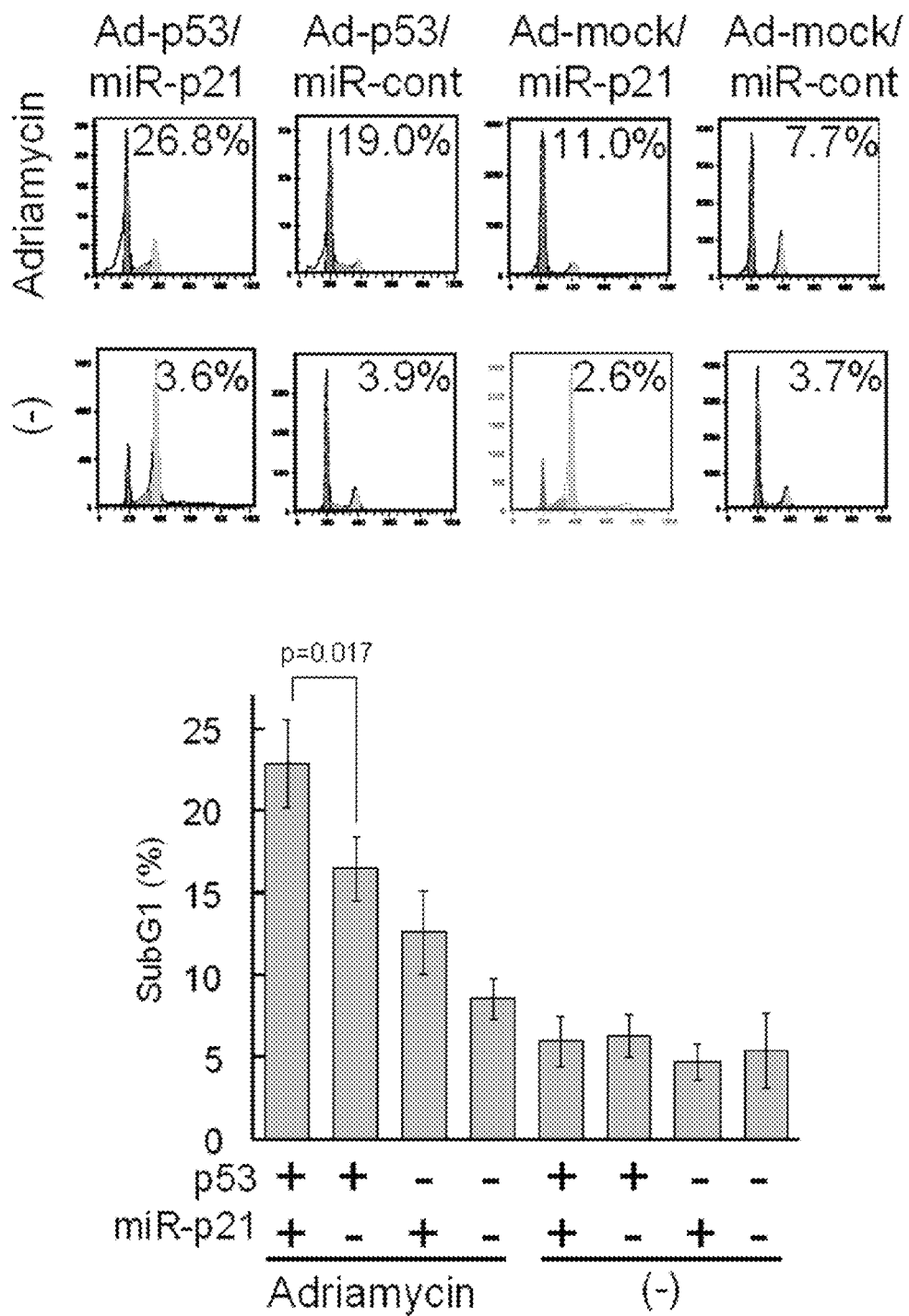

FIG. 15 shows the proportion of cells undergoing apoptosis among cells treated by a recombinant adenovirus expressing p53 together with p21-specific miRNAs. Cellular DNA content was analyzed by flow cytometry. The percentage of cells in sub-G1 is indicated (top). The average of three independent experiments is also indicated (bottom). Error bars indicate S.E., and p values were calculated by Student's t testing.

FIG. 16 shows the therapeutic effect of adenovirus-mediated expression of p53 together with p21-specific miRNAs in an in vivo xenograft model of tumorigenesis. SW480 and DLD1 cells were injected s.c. into nude mice. When a tumor volume reached 100 mm$^3$, the indicated adenovirus vectors were injected directly into the tumors at days 0, 1 and 2 (indicated by arrows). Ad-p53/miR-p21, closed circle; Ad-p53/miR-control, open circle; Ad-mock/miR-p21, closed square; and Ad-mock/miR-control, open square. The data represent the average volume of three independent tumors injected with adenovirus. The volume of each tumor is expressed relative to the volume at day 0, which was set as 1. Error bars indicate S.E., and p-values were calculated by Student's t testing.

DESCRIPTION OF EMBODIMENTS

Unless otherwise stated in the present specification, scientific and technical terms used with respect to the present invention have the meaning normally understood by a person skilled in the art. In general, terms and techniques used with respect to cell and tissue culturing, molecular biology, immunology, microbiology, gene, protein, and nucleic acid chemistry, and hybridization described in the present specification are well known in the art and normally used. In general, unless otherwise stated, the methods and techniques of the present invention are carried out in accordance with standard methods well known in the art and as described in various general and specialized publications referred to or discussed in the present specification. Such publications include, for example, Sambrook et al., Molecular Cloning: A Laboratory Manual, 2d ed., Cold Spring Harbor Laboratory Press (1989) and Sambrook et al., Molecular Cloning: A Laboratory Manual, 3d ed., Cold Spring Harbor Press (2001); Ausubel et al., Current Protocols in Molecular Biology, Greene Publishing Associates (1992, and supplement in 2000); Ausubel et al., Short Protocols in Molecular Biology: A Compendium of Methods from Current Protocols in Molecular Biology—4th Ed., Wiley & Sons (1999); Harlow and Lane, Antibodies: A Laboratory Manual, Cold Spring Harbor Laboratory Press (1990); and Harlow and Lane, Using Antibodies: A Laboratory Manual, Cold Spring Harbor Laboratory Press (1999), etc., all of which are hereby incorporated herein by reference in their entireties.

Enzyme reactions and purification techniques are carried out in accordance with manufacturer-supplied specifications and as normally carried out in the art or as described in the present specification. Terms, experimental procedures, and techniques used with respect to analytical chemistry, synthetic organic chemistry, medicinal chemistry, and pharmaceutical chemistry described in the present specification are well known in the art and normally used. Standard techniques are employed in chemical synthesis, chemical analysis, production, formulation, and delivery of an agent, and treatment of a subject.

The singular forms "a", "and", and "the" are used herein to include plural referents unless the context clearly dictates otherwise. Other than in the Examples, or where otherwise indicated, all numbers expressing quantities of ingredients, reaction conditions, and so forth used in this application are to be understood as being modified in all instances by the term "about." Accordingly, unless the contrary is indicated, the numerical parameters set forth in this application are approximations that may vary depending upon the desired properties sought to be obtained by the present invention. Furthermore, unless otherwise indicated, the terms "protein", "peptide" and "polypeptide" are used interchangeably.

In the present invention, there is provided an agent, a composition or a product that includes an apoptosis-inducing substance and a substance that inhibits expression and/or activity of an apoptosis-inhibiting substance.

As used herein, an apoptosis-inducing substance includes any substance that is capable of inducing apoptosis in a cell, and encompasses, but is not limited to, at least one small molecule, and/or protein and nucleic acid molecule encoding said protein. Small molecules capable of inducing apoptosis include, but are not limited to, doxorubicin, platinum complexes such as carboplatin, cisplatin, and nedaplatin. In one embodiment, the apoptosis-inducing small molecule used in the present invention induces apoptosis via induction of an apoptosis-inducing protein as defined below.

The apoptosis-inducing protein used in the present invention includes, but is not limited to, p53 family protein such as p53, p63, p73, and isoform, chimera and functional fragment thereof. The nucleic acid sequence of human p53, p63 and p73 is available at GenBank database (http://www.ncbi.nlm.nih.gov/) as accession numbers NM_000546, NM_003722 and NM_005427, respectively. The nucleic acid sequence of p53 is also represented herein as SEQ ID NO:9. The sequence of other animals may also be found in publicly available databases such as GenBank: NM_001003210 (p53 of dog), NM_001009294 (p53 of cat), XM_545249 (p63 of dog), AY069989 (p73 of dog).

The proteins of a p53 family are present in various isoforms mainly due to splicing, such as p53 beta, gamma, p73 alpha, beta, gamma, delta, epsilon, theta, zeta, eta, p63 alpha, beta, gamma, all of which are included in the apoptosis-inducing protein used in the present invention. In addition, the proteins of a p53 family share highly homologous domains, i.e., the transactivation domain (TA), the DNA-binding domain (DBD) and the oligomerization domain (OD), which involve in the function of proteins (see, e.g., Stiewe, Nat Rev Cancer. 2007; 7(3):165-8). Thus, the apoptosis-inducing protein used in the present invention also includes functional fragments of the proteins of a p53 family that comprise the transactivation domain, DNA-binding domain and oligomerization domain. The functionality of a functional fragment may be assayed by detecting a gene which is normally induced by a full length protein, such as p21, SFN, Gadd45, BTG2, CAV1, DUSP5, EGFR, HGF, MET, PCNA, PLAGL1, SESN1, SH2D1A, TGFA, PCBP4, RRM2B, STEAP3, ARID3A, C13orf15, CCNG1, CCNK, DDB2, DDIT4, GML, GPX1, HRAS, IBRDC2, MET, MSH2, PLK2, RB1, S100A2, TP53i3, TRIM22 and VCAN, in case of p53.

The apoptosis-inducing protein used in the present invention also includes chimera proteins of the p53 family (see, e.g., JP 2000-354488 A). These chimera proteins comprise a transactivation domain of any single p53 family member, a DNA-binding domain of any single same or other p53 family member, and an oligomerization domain of any single same or other p53 family member. Each domain used in these chimeras may be derived either from a same protein or different proteins of a p53 family. For instance, a chimera protein may include a transactivation domain of p53, a DNA-binding domain of p63, and an oligomerization domain of p73, and so on.

As used herein, the apoptosis-inducing protein is intended to include a functional mutant thereof selected from the group consisting of:
i) a polypeptide having an amino acid sequence with one or more, or one or a few mutations in the amino acid sequence of the apoptosis-inducing protein, but still being capable of inducing apoptosis;
ii) a polypeptide encoded by a nucleic acid molecule hybridizing under stringent conditions with a nucleic acid molecule encoding the apoptosis-inducing protein, a complementary strand thereof or a fragment thereof, and being capable of inducing apoptosis; and
iii) a polypeptide being at least 60%, at least 70%, at least 80%, at least 90% or at least 95% homologous to the amino acid sequence of the apoptosis-inducing protein, and being capable of inducing apoptosis.

Similarly, the nucleic acid molecule encoding an apoptosis-inducing protein is intended to include a functional mutant thereof selected from the group consisting of:
i) a nucleic acid molecule having a nucleotide sequence with one or more, or one or a few mutations in the nucleotide sequence encoding the apoptosis-inducing protein, but still encoding a polypeptide capable of inducing apoptosis;
ii) a nucleic acid molecule hybridizing under stringent conditions with a nucleic acid molecule encoding the apoptosis-inducing protein, a complementary strand thereof or a fragment thereof, and encoding a polypeptide capable of inducing apoptosis; and iii) a nucleic acid molecule being at least 60%, at least 70%, at least 80%, at least 90% or at least 95% homologous to the nucleotide sequence encoding the apoptosis-inducing protein, and encoding a polypeptide capable of inducing apoptosis.

The term 'stringent conditions' used herein refers to parameters that are well known in the art. Parameters for the hybridization of a nucleic acid are described in standard protocols such as, for example, Sambrook et al., Molecular Cloning: A Laboratory Manual, 3d ed., Cold Spring Harbor Press (2001), or Ausubel et al., Current Protocols in Molecular Biology, Greene Publishing Associates (1992).

Specifically, the stringent conditions used in the present specification mean hybridization at 65 degree C. by means of a hybridization buffer containing 3.5×SSC, Ficoll 0.02%, polyvinylpyrrolidone 0.02%, bovine serum albumin 0.02%, $NaH_2PO_4$ 25 mM (pH7), SDS 0.05%, and EDTA 2 mM. Among the above-mentioned components, SSC is 0.15 M sodium chloride/0.15 M sodium citrate at pH 7, SDS is sodium dodecylsulfate, and EDTA is ethylenediaminetetraacetic acid. After the hybridization, a membrane to which DNA is transferred is washed with 2×SSC at room temperature, then with 0.1 to 0.5×SSC/0.1×SDS at a temperature up to 68 degree C. Alternatively, the stringent hybridization may employ hybridization and washing conditions described by a manufacturer using a commercial hybridization buffer such as an ExpressHyb® buffer solution (manufactured by Clontech Corp.).

There are other conditions, reagents, etc. that can be used and give the same degree of stringency, but since it can be expected that a person skilled in the art knows such conditions very well, there is no particular description thereof in the present specification. However, it is possible to manipulate the conditions so that a homologue or an allelic gene of a nucleic acid that codes for the mutant of the nucleic acid molecule or protein of interest can be clearly identified.

The apoptosis-inducing properties of an apoptosis-inducing substance to be used in the present invention may be evaluated by any appropriate methods including, but are not limited to, comparing the degree of apoptosis or the proportion of cell undergoing apoptosis with or without the candidate substance. The degree of apoptosis may be evaluated, e.g., by measurement of caspase-3 activity, and the proportion of cell undergoing apoptosis may be evaluated, e.g., by measurement of proportion of cell in sub-G1 (see Examples).

As used herein, an apoptosis-inhibiting substance includes any protein that is capable of inhibiting apoptosis in a cell. In one embodiment, the apoptosis-inhibiting substance is a substance that inhibits apoptosis induced by an apoptosis-inducing protein, in particular, by a p53 family protein as well as isoform, chimera and functional fragment thereof as defined above. Therefore, the apoptosis-inhibiting substance in this embodiment may be selected from the group consisting of a protein involved in cell cycle arrest, an ubiquitin ligase and a dominant negative variant of a p53 family protein.

A protein involved in cell cycle arrest includes, but is not limited to, p21 (NM_000389), SFN (stratifin, 14-3-3 sigma, NM_006142), Gadd45 (NM_001924), p300 (EP300, NM_001429), BTG2 (TIS21, NM_006763), CAV1 (NM_001753), DUSP5 (NM_004419), EGFR(NM_005228), HGF (SF, NM_000601), MET (NM_000245), PCNA (NM_002592), PLAGL1 (ZAC, BC074814), SESN1 (PA26, AF033120), SH2D1A (SAP, NM_002351), TGFA (NM_003236), PCBP4 (NM_020418), RRM2B (NM_015713), STEAP3 (NM_001008410), ARID3A (E2FBP1, NM_005224), C13orf15 (RGC32, NM_014059), CCNG1 (NM_004060), CCNK (NM_003858), DDB2 (NM_000107), DDIT4 (REDD1, NM_019058), GML (NM_002066), GPX1 (NM_000581), HRAS (c-Ha-Ras, NM_176795), IBRDC2 (NM_182757), MET (NM_000245), MSH2 (NM_000251), PLK2 (SNK, NM_006622), RB1 (NM_000321), S100A2 (NM_005978), TP53i3 (Pig3, NM_004881), TRIM22 (Staf50, NM_006074), VCAN (CSPG2, NM_004385) (see Riley et al., Nat Rev Mol Cell Biol. 2008; 9(5):402-12, in particular its supplementary information. The number in parenthesis indicates GenBank accession number). In one embodiment, the protein involved in cell cycle arrest is selected from the group consisting of p21, SFN, Gadd45 and p300.

Ubiquitin ligase used in the present invention includes, but is not limited to MDM2 (GenBank accession Nos.: NM_002392, NM_006878, NM_006879, NM_006881, NM_006882). Dominant negative variant of a p53 family protein used in the present invention includes variant of a p53 family protein which has mutation in transactivation domain, DNA-binding domain and/or oligomerization domain, in particular in DNA-binding domain. In one embodiment, dominant negative variant of a p53 family protein includes, but is not limited to, human p53 having the following mutation: G117E, P152T, T155I, R156P, R175H, P177S, P177F, P177H, H179Y, E180K, R181G, R181H, N239S, S241T, S241F, C242Y, G244S, G245S, G245D, M246L, P250L, L257P, D259V, R273C, R273H, V274F, G279E, G279V, G279R, D281N, D281E, R282Q, E286K (see Willis et al., Oncogene 2004; 23:2330-8, Blagosklonny et al., Faseb J 2000; 14:1901-7, Monti et al., Oncogene 2002; 21:1641-8.).

In one embodiment, the apoptosis-inhibiting substance is induced by the action of the apoptosis-inducing substance. Examples of such apoptosis-inhibiting substance include, but are not limited to p21, SFN, Gadd45, BTG2, CAV1, DUSP5, EGFR, HGF, MET, PCNA, PLAGL1, SESN1, SH2D1A, TGFA, PCBP4, RRM2B, STEAP3, ARID3A, C13orf15, CCNG1, CCNK, DDB2, DDIT4, GML, GPX1, HRAS, IBRDC2, MET, MSH2, PLK2, RB1, S100A2, TP53i3, TRIM22 and VCAN, all of which are induced by p53.

The apoptosis-inhibiting properties of an apoptosis-inhibiting substance to be used in the present invention may be evaluated by any appropriate methods including, but being not limited to, comparing the degree of apoptosis or the proportion of cell undergoing apoptosis with or without the candidate substance under apoptotic condition. Apoptotic condition includes, but is not limited to, exposure to apoptosis-inducing stimuli such as irradiation, treatment by apoptosis-inducing substance such as doxorubicin and platinum complex, expression of apoptosis-inducing protein such as p53 family protein. The degree of apoptosis may be evaluated, e.g., by measurement of caspase-3 activity, and the proportion of cell undergoing apoptosis may be evaluated, e.g., by measurement of proportion of cell in sub-G1 (see Examples).

Therefore, a substance that inhibits expression and/or activity of an apoptosis-inhibiting substance used in the present invention includes, but is not limited to, a nucleic acid molecule that inhibits expression of an apoptosis-inhibiting substance as defined above, such as an antisense nucleic acid, ribozyme, aptamer and RNAi effector such as miRNA, shRNA and siRNA directed to the apoptosis-inhibiting substance, as well as a nucleic acid molecule that encodes such nucleic acid molecule.

In one embodiment, a substance that inhibits activity of an apoptosis-inhibiting substance includes, but is not limited to, a substance that binds to the apoptosis-inhibiting substance such as an antibody, a dominant negative variant of the apoptosis-inhibiting substance, an antagonist of the apoptosis-inhibiting substance such as a substance that binds to the target or receptor of the apoptosis-inhibiting substance.

The ability of a substance to inhibit expression and/or activity of an apoptosis-inhibiting substance may be evaluate using conventional method, e.g., by comparing the expression and/or activity of the apoptosis-inhibiting substance with or without the test substance, and if the expression and/or activity of the apoptosis-inhibiting substance in the presence of the test substance is increased compared to that in the absence of the test substance, said test substance is regarded as a substance that inhibits expression and/or activity of the apoptosis-inhibiting substance.

RNAi effector is a substance that inhibits expression of the target gene by RNA interference (RNAi). RNAi is a widely used technique for the suppression of a specific target gene (Hannon et al., Nature 2002; 418:244-51, Rana et al., Nat Rev Mol Cell Biol 2007; 8:23-36). RNAi effector includes, but is not limited to, small interfering RNA (siRNA), short hairpin RNA (shRNA) and Micro-RNA (miRNA). SiRNA is a double-stranded RNA oligonucleotide, which can be transfected directly into cells. ShRNA, which are expressed using a vector-based expression system, has a short length structure like G-N18-Loop-N'18-C without 5'-cap and polyA tail (Brummelkamp et al., Science 2002; 296:550-3, Paddison et al., Genes Dev 2002; 16:948-58, Paul et al., Nat Biotechnol 2002; 20:505-8). For the expression of shRNA in which the length of transcript must be strictly regulated, pol III promoter which can regulate the length of transcript is preferred. MiRNA is a third type of RNAi system, which is transcribed as a long mRNA (pri-miRNA) with 5'-cap and polyA tail like a transcript of coding genes (Ambros et al., Nature 2004; 431:350-5, Ambros et al., Cell 2001; 107:823-6). Therefore, various promoters such as pol II and pol III promoters are available for the expression of miRNA by a vector.

The miRNA has several advantageous features. First, ORF can be incorporated into the miRNA vector such that the pre-miRNA insertion site is in the 3' UTR of the coding sequence. Pol II promoter enables co-cistronic expression of a protein of interest and an artificial miRNA engineered to suppress a specific target gene in mammalian cells. Using this system, it is possible to express an apoptosis-inducing protein such as p53 and miRNA specific to an apoptosis-inhibiting protein simultaneously from a single vector. In this manner, the possible negative effect resulting from the suppression of the apoptosis-inhibiting protein in the absence of expression of the apoptosis-inducing protein can be avoided. For example, it is possible to circumvent the risk of cancer cell proliferation by a protein involved in cell cycle arrest in the absence of expression of a p53 family protein.

The second advantage of miRNA is that multiple miRNA sequences can be inserted in tandem in a single nucleic acid construct or vector. This feature enables co-cistronic expression of multiple mRNAs from a single construct. Actually, some endogenous miRNAs are expressed in clusters in long primary transcripts driven by Pol II promoter. Accordingly, it is possible to insert different miRNA sequences into a single vector to achieve a synergistic effect. The third advantage is that an miRNA plasmid vector can readily be converted into a recombinant adenoviral vector, thus providing a versatile system for therapeutic applications.

miRNA for a specific protein may be designed based on the base sequence thereof obtained from the database or its Accession Number, using BLOCK-iT RNAi Designer from Invitrogen (https://rnaidesigner.invitrogen.com/rnaiexpress/).

A double-strand polynucleotide formed from RNA and DNA that inhibits the expression of a target gene described in JP, A, 2003-219893 may be mentioned as another type of RNAi system. This polynucleotide may be a DNA/RNA hybrid in which one of two strands is DNA and the other is RNA, or a DNA/RNA chimera in which one portion of the same strand is DNA and the other portion is RNA. Such a polynucleotide is preferably formed from 19 to 25 nucleotides, more preferably 19 to 23 nucleotides, and yet more preferably 19 to 21 nucleotides; in the case of the DNA/RNA hybrid, it is preferable that the sense strand is DNA and the antisense strand is RNA, and in the case of the DNA/RNA chimera, it is preferable that one portion on the upstream side of the double-strand polynucleotide is RNA. Such a polynucleotide may be prepared so as to have any sequence in accordance with a chemical synthetic method known per se.

In case of a nucleic acid molecule that inhibits expression of a dominant negative variant of a p53 family protein, the nucleic acid molecule may target the coding region of the protein, but it is also possible to target the non-coding region of the protein, in particular 3' UTR of a p53 family mRNA, so that all the endogenous dominant negative protein is specifically knocked-down, while exogenous wild-type p53 family protein which would contain only the coding region, expressed from the agent, composition or product of the present invention remains intact.

As used herein, the nucleic acid molecule that inhibits expression of an apoptosis-inhibiting substance is intended to include a functional mutant thereof selected from the group consisting of:

i) a nucleic acid molecule having a nucleotide sequence with one or more, or one or a few mutations in the nucleotide sequence of the nucleic acid molecule that inhibits expression of an apoptosis-inhibiting substance, but still being capable of inhibiting expression of an apoptosis-inhibiting substance;

ii) a nucleic acid molecule hybridizing under stringent conditions with the nucleic acid molecule that inhibits expression of an apoptosis-inhibiting substance, a complementary strand thereof or a fragment thereof, and being capable of inhibiting expression of an apoptosis-inhibiting substance; and iii) a nucleic acid molecule being at least 60%, at least 70%, at least 80%, at least 90% or at least 95% homologous to the nucleotide sequence of the nucleic acid molecule that inhibits expression of an apoptosis-inhibiting substance, and being capable of inhibiting expression of an apoptosis-inhibiting substance.

In the present invention, the apoptosis-inducing substance and the substance that inhibits expression and/or activity of an apoptosis-inhibiting substance may be combined in any way. In one embodiment, the apoptosis-inhibiting substance inhibits apoptosis induced by the apoptosis-inducing substance. For example, if the apoptosis-inducing substance is p53, the apoptosis-inhibiting substance may be selected from the group consisting of a protein involved in cell cycle arrest related to p53 such as p21, SFN, Gadd45, p300, BTG2, CAV1, DUSP5, EGFR, HGF, MET, PCNA, PLAGL1, SESN1, SH2D1A, TGFA, PCBP4, RRM2B, STEAP3, ARID3A, C13orf15, CCNG1, CCNK, DDB2, DDIT4, GML, GPX1, HRAS, IBRDC2, MET, MSH2, PLK2, RB1, S100A2, TP53i3, TRIM22 and VCAN, an ubiquitin ligase related to p53 such as MDM2 and a dominant negative variant of a p53 family protein.

The agent, composition or product of the present invention may comprise at least one apoptosis-inducing substance, and at least one substance that inhibits expression and/or activity of an apoptosis-inhibiting substance. For example, the agent, composition or product of the present invention may comprise at least one p53 family protein and/or nucleic acid molecule encoding it. In one embodiment, the agent, composition or product of the present invention comprise at least one substance that inhibits expression and/or activity of a protein involved in cell cycle arrest as a substance that inhibits expression and/or activity of an apoptosis-inhibiting substance. In another embodiment, the agent, composition or product of the present invention comprise at least one substance that inhibits expression and/or activity of an ubiquitin ligase and/or of a dominant negative variant of a p53 family protein, in addition to at least one substance that inhibits expression and/or activity of a protein involved in cell cycle arrest as a substance that inhibits expression and/or activity of an apoptosis-inhibiting substance.

In one embodiment, the agent, composition or product of the present invention comprise at least one substance that inhibits expression and/or activity of p21, SFN, Gadd45 and/or p300. In another embodiment, the agent, composition or product of the present invention comprise at least one substance that inhibits expression and/or activity of MDM2 and/or of a dominant negative variant of a p53 family protein in addition to at least one substance that inhibits expression and/or activity of p21, SFN, Gadd45 and/or p300.

The agent, composition or product of the present invention may be used as an apoptosis inducer or for the treatment of a proliferative disease. As used herein, a proliferative disease is intended to mean any condition in which abnormal proliferation of cells is involved, and includes, but is not limited to benign or malignant tumor, hyperplasia, keloid, Cushing syndrome, primary aldosteronism, erythroplakia, polycythemia vera, leukoplakia, hyperplastic scar, lichen planus and lentiginosis. In this embodiment, the agent, composition or product of the present invention may further comprise other active substance useful to treat the corresponding disease, such as anti-tumor agent, anti-inflammatory agent, vitamins, etc.

The anti-tumor agent that may be use in the present invention includes, but is not limited to, alkylating agents such as ifosfamide, nimustine, cyclophosphamide, dacarbazine, melphalan, and ranimustine, antimetabolites such as gemcitabine, enocitabine, cytarabine, tegafur/uracil, a tegafur/gimeracil/oteracil mixture, doxifluridine, hydroxycarbamide, fluorouracil, methotrexate, and mercaptopurine, antitumor antibiotics such as idarubicin, epirubicin, daunorubicin, doxorubicin, pirarubicin, bleomycin, peplomycin, mitoxantrone, and mitomycin C, alkaloids such as etoposide, irinotecan, vinorelbine, docetaxel, paclitaxel, vincristine, vindesine, and vinblastine, hormone therapy agents such as anastrozole, tamoxifen, toremifene, bicalutamide, flutamide, and estramustine, platinum complexes such as carboplatin, cisplatin, and nedaplatin, angiogenesis inhibitors such as thalidomide, neovastat, and bevacizumab, L-asparaginase etc.

The anti-inflammatory agent that may be use in the present invention includes, but is not limited to, a steroidal anti-inflammatory drug, such as prednisolone, beclomethasone, betamethasone, fluticasone, dexamethasone and hydrocortisone, a non-steroidal anti-inflammatory drug, such as acetylsalicylic acid, loxoprofen, acetaminophen, ketoprofen, tiaprofenic acid, suprofen, tolmetin, carprofen, benoxaprofen, piroxicam, benzydamine, naproxen, diclofenac, ibuprofen, diflunisal, and azapropazone, a substance that inhibits the expression of an inflammatory cytokine, such as antisense nucleic acid, ribozyme, aptamer and RNAi effector against the inflammatory cytokine gene, and a substance that inhibits activities of an inflammatory cytokine, such as antibodies against the inflammatory cytokine, and receptor antagonist of a receptor of the inflammatory cytokine.

The vitamins that may be use in the present invention includes, but are not limited to, VA (retinol), $VB_1$ (thiamine), $VB_2$ (riboflavin), $VB_3$ (niacin), $VB_5$ (pantothenic acid), $VB_6$ (pyridoxine), $VB_7$ (biotin), $VB_9$ (folic acid), $VB_{12}$ (cyanocobalamin), VC (ascorbic acid), VD (calciferol), VE (tocopherol) and VK (phylloquinone) as well as derivatives and analogs thereof.

The agent, composition or product of the present invention may be presented in any suitable form depending on the use thereof, and active substances contained therein, i.e., the apoptosis-inducing substance and the substance that inhibits expression and/or activity of the apoptosis-inhibiting substance, and optional active substance. For example, all the active substances may be contained in and/or attached to a suitable carrier such as polymer micelle, liposome, emulsion, microsphere, and nanosphere. Such form is particularly suitable if at least one substance is a small molecule or polypeptide. If all the active substances are nucleic acid molecules, it is possible to incorporate them in at least one nucleic acid construct or vector. In such a case, the nucleic acid molecules may be positioned in tandem in a single expression cassette, so that the expression is controlled by a same regulatory sequence such as promoter(s) or enhancer(s). In one embodiment, the nucleic acid molecules may be expressed as a single primary transcript. In one embodiment, the nucleic acid molecules may be expressed co-cistronically.

When used in the present specification, the 'vector' means any nucleic acid that is capable of introducing a desired nucleic acid molecule by digestion or ligation in order to transfer between different genetic environments or in order to carry out expression in a host cell. The vector is typically constituted from DNA, but an RNA vector may also be used. The vector includes a plasmid, a phagemid, and a virus genome, but should not be limited thereto. A cloning vector can replicate in a host cell autonomously or after integration into a genome and is further characterized by one or more endonuclease restriction sites, the vector is cleaved in a decidable manner at these sites, a desired nucleic acid sequence can be linked thereto, and a novel recombinant vector can thereby replicate a target nucleic acid molecule in a host. In the case of a plasmid, by increasing the plasmid copy number in the host bacterium, a desired nucleic acid molecule may be replicated any number of times, or replication may be carried out only once per host before the host is regenerated by cell division. In the case of a phage, replication may occur actively between lytic phases, or may occur passively between lysogenic phases.

With regard to an expression vector, a desired nucleic acid sequence is inserted thereinto by digestion and ligation, operably linked to a regulatory sequence, and expressed as a transcript.

The gene used in the present invention may be constituted from one or more genes, and when it is constituted from two or more genes, these genes may be inserted into a single expression vector or may be inserted separately into two or more vectors. The expression vector may further contain one or more marker sequences that are suitable for identifying a cell that is or is not transformed or transfected by the vector. The marker contains, for example, a gene that codes for a protein that increases or decreases either the resistance or the sensitivity toward an antibiotic or another compound, a gene that codes for an enzyme (e.g. beta-galactosidase, luciferase, or alkaline phosphatase) whose activity is detectable by a standard analytical method in the art, and a gene that visually affects the phenotype of a transformed or transfected cell, a host, a colony, or a plaque. A preferred expression vector is a vector that enables autonomous replication and expression of a structural gene product present in a DNA segment to which the vector is operably linked.

In the present specification, the code sequence and the regulatory sequence are said to be 'operably' linked when they are linked in a manner in which expression or transcription of the code sequence is under the influence or control of the regulatory sequence. If it is desired that the code sequence is translated into a functional protein, the two DNA sequences are said to be 'operably' linked if, as a result of induction by a promoter in a 5' regulatory sequence, transcription of the code sequence occurs, or if linkage properties between the two DNA sequences (1) do not result in induction of frameshift mutation, (2) do not interfere in the ability of the promoter for instructing transcription of the code sequence, or (3) do not interfere in the ability of a corresponding RNA transcript to be translated into a protein. Therefore, the promoter region is operably linked to the code sequence if the promoter region can transcribe the DNA sequence so that the resulting transcript is translated into a desired protein or polypeptide.

An useful vector in the present invention contains a nucleic acid molecule that codes for an apoptosis-inducing protein and a substance that inhibits expression and/or activity of an apoptosis-inhibiting substance as defined above that functionally binds to an appropriate transcriptional or translational regulatory sequence that is derived from a gene of, for example, a mammal, a microbe, a virus, or an insect as desired. Such a regulatory sequence includes a sequence having a regulatory role in gene expression such as, for example, a transcription promoter or enhancer, an operator sequence for regulating transcription, a sequence that codes for a ribosome-binding site within a messenger RNA, and an appropriate sequence that regulates transcription, translation initiation, or transcription termination.

Detailed properties of the regulatory sequence necessary for gene expression may be different depending on the species of organism or species of cell, but it can generally contain at least 5' nontranscribed and 5' untranslated sequences involved in initiation of transcription and translation, such as a TATA box, a capping sequence, and a CAAT sequence. In particular, such a 5' nontranscribed regulatory sequence can contain a promoter region that contains a promoter sequence for regulating the transcription of an operably linked gene. The regulatory sequence also contains an enhancer sequence or a desired upstream activator sequence. The vector of the present invention may optionally contain a 5' leader or signal sequence. Selection and design of an appropriate vector are within the ability and freedom of a person skilled in the art.

A particularly useful regulatory sequence contains a promoter region derived from a gene of various mammals, viruses, microbes, and insects. This promoter region commands initiation of the transcription of a target gene, thus resulting in transcription of the whole DNA containing the gene of interest. An useful promoter region includes a CAG promoter, a retroviral LTR promoter, a cytomegalovirus (CMV) enhancer/promoter region, an RSV LTR promoter, a lac promoter, and a promoter isolated from an adenovirus, but any other promoters known to a person skilled in the art that are useful for gene expression in a eucaryote, a procaryote, a virus, or a microbial cell may be used.

Other particularly useful promoters for expressing a gene or a protein within a eucaryote cell include mammalian cell promoter and enhancer sequences such as, for example, those induced from polyomavirus, adenovirus, SV40 virus, and human cytomegalovirus. Typically, virus early and late promoters, which are found adjacent to the virus replication origin of a virus such as SV40, are particularly useful. Selection of a specific useful promoter depends on various other parameters pertaining to the cell line and the nucleic acid construct used for expressing the protein or nucleic acid of interest within a specific cell line. Furthermore, any promoter that is known to express a gene in a target cell at a sufficiently high level to be useful in the present invention may be selected.

The nucleic acid construct of the present invention therefore includes various forms of the nucleic acid molecule of interest that are operably linked to either of the promoter sequence or the promoter and enhancer sequence, and that are further functionally linked to a polyadenylation sequence that commands termination and polyadenylation of mRNA. The nucleic acid construct of the present invention can contain another gene sequence that enables efficient replication and expression of the construct within a desired cell. Such a sequence can include an intron derived from a viral gene, etc.

The agent, composition or product of the present invention may be administered via various routes including oral and parenteral routes; examples thereof include, but are not limited to, oral, intravenous, intramuscular, subcutaneous, local, rectal, intratumoral, intraarterial, intraportal, intraventricular, transmucosal, percutaneous, intranasal, intraperitoneal, intrapulmonary, and intrauterine routes, and the medicine may be prepared in a form appropriate for each administration route. Such a form and a preparation method may employ any known form and method as appropriate (see, e.g. 'Hyoujun Yakuzaigaku' (Standard Pharmaceutics), Ed. Y. Watanabe et al., Nankodo, 2003, etc.).

Examples of forms suitable for oral administration include, but are not limited to, powder, granule, tablet, capsule, liquid, suspension, emulsion, gel, and syrup, and examples of forms suitable for parenteral administration include injections such as injectable solution, injectable suspension, injectable emulsion, and an on-site preparation type injection. The formulation for parenteral administration may be in the form of an aqueous or nonaqueous isotonic sterile solution or suspension.

In another aspect of the present invention, there is provided an apoptosis induction method comprising a step of introducing into cells an apoptosis-inducing substance and a substance that inhibits expression and/or activity of an apoptosis-inhibiting substance. This method may be carried out in vitro, ex vivo or in vivo. Thus, the cells may be isolated from a subject, or may be present in a subject.

In another aspect of the present invention, there is provided a method for treating a proliferative disease comprising a step of administrating a therapeutically effective amount of an apoptosis-inducing substance and a substance that inhibits expression and/or activity of an apoptosis-inhibiting substance to a subject in need thereof.

In these aspects of the invention, the meaning of the apoptosis-inducing substance, the substance that inhibits expression and/or activity of the apoptosis-inhibiting substance used herein, as well as of the proliferative disease is as defined above for the agent, composition and product of the present invention.

In one embodiment, the apoptosis-inducing substance and the substance that inhibits expression and/or activity of the apoptosis-inhibiting substance are contained in any of the agent, composition or product of the present invention as defined above.

Furthermore, a method of introduction in the above-mentioned method is not limited, and any known method of introduction such as, for example, a calcium phosphate method, a lipofection method, an ultrasonic introduction method, an electroporation method, a particle gun method, a method employing a virus vector such as an adenovirus vector or a retrovirus vector, or a microinjection method may be used.

In the method for treating a proliferative disease, the agent, composition or product of the present invention may be administrated alone or in combination with other active substance useful to treat the corresponding disease, such as anti-tumor agent, anti-inflammatory agent, vitamins, etc., which are exemplified above. In case of combined administration, the agent, composition or product of the present invention may be administrated prior to, at the same time as, or after the administration of the other active substance.

The effective amount referred to here is an amount that suppresses onset of the target disorder, reduces symptoms thereof, or prevents progression thereof, and is preferably an amount that prevents onset of the target disorder or cures the target disorder. It is also preferably an amount that does not cause an adverse effect that exceeds the benefit from administration. Such an amount may be determined as appropriate by an in vitro test using cultured cells, etc. or by a test in a model animal such as a mouse, a rat, a dog, or a pig, and such test methods are well known to a person skilled in the art.

The dosage of the active substances administered by the method of the present invention depends on the type of drug used. The dosage of the active substances, agent, composition or product used in the method of the present invention are either known to a person skilled in the art or are determined as appropriate by the above-mentioned test, etc. For instance, in case of an adenoviral vector, the dose range may be $1\times10^3$ to $1\times10^{14}$, or $1\times10^4$ to $1\times10^{13}$, or $1\times10^5$ to $1\times10^{12}$, or $1\times10^6$ to $1\times10^{11}$, or $1\times10^7$ to $1\times10^{10}$ plaque forming units (p.f.u.) per human subject.

A specific dosage of a medicine administered in the method of the present invention can be determined while taking into consideration various conditions of a subject that requires treatment, for example, the severity of symptoms, general health conditions of the subject, age, weight, sex of the subject, diet, the timing and frequency of administration, a medicine used in combination, responsiveness to treatment, and compliance with treatment, and it might be different from the above-mentioned typical dosage, but in such a case, these methods are still included in the scope of the present invention.

With regard to the administration route, there are various routes including both oral and parenteral routes such as, for example, oral, intravenous, intramuscular, subcutaneous, local, rectal, intratumoral, intraarterial, intraportal, intraventricular, transmucosal, percutaneous, intranasal, intraperitoneal, intrapulmonary, and intrauterine routes.

The frequency of administration depends on the properties of the medicine used and the above-mentioned conditions of the subject and may be, for example, a plurality of times a day (i.e. 2, 3, 4, 5, or more times per day), once a day, every few days (i.e. every 2, 3, 4, 5, 6, or 7 days, etc.), once a week, or once every few weeks (i.e. once every 2, 3, or 4 weeks, etc.).

In the method of the present invention, the term 'subject' means any living individual, preferably an animal, more preferably a mammal, and yet more preferably a human individual. In the present invention, the subject may be healthy or affected with some disorder, and in the case of treatment of a disorder being intended, the subject typically means a subject affected with the disorder or having a risk of being affected.

Furthermore, the term 'treatment' includes all types of medically acceptable prophylactic and/or therapeutic intervention for the purpose of the cure, temporary remission, prevention, etc. of a disorder. For example, when the disorder is proliferative disease, the term 'treatment' includes medically acceptable intervention for various purposes including delaying or halting the progression thereof, regression or disappearance of lesions, prevention of the onset of the disease, or prevention of recurrence thereof.

The above-mentioned agent, composition, product and method may be used particularly advantageously when apoptosis is induced in cells that are resistant to apoptosis by an apoptosis-inducing protein.

In another aspect of the invention, there is provided a nucleic acid construct comprising:
a nucleic acid molecule encoding a protein to be expressed, and
a nucleic acid molecule which inhibits expression of an undesired protein.

In one embodiment, the protein to be expressed is an apoptosis-inducing protein as defined above. In one embodiment, the apoptosis-inducing protein is preferably a protein of a p53 family. In one embodiment, the undesired protein is an apoptosis-inhibiting protein as defined above. In one embodiment, the apoptosis-inhibiting protein is selected from the group consisting of a protein involved in cell cycle arrest, an ubiquitin ligase and a dominant negative variant of a p53 family protein as defined above. In one embodiment, the nucleic acid molecule encoding a protein to be expressed and the nucleic acid molecule which inhibits expression of an undesired protein are operably linked to a same regulatory sequence such as promoter(s) and enhancer(s). In one embodiment, the nucleic acid molecule encoding a protein to be expressed and the nucleic acid molecule which inhibits expression of an undesired protein are expressed as a single primary transcript. In one embodiment, the nucleic acid molecule encoding a protein to be expressed and the nucleic acid molecule which inhibits expression of an undesired protein are expressed co-cistronically. In a preferred embodiment, the nucleic acid molecules may be positioned in tandem in a single expression cassette, so that the expression is controlled by a same promoter. These configurations are advantageous in case that the expression of only either one nucleic acid molecule may have deleterious effect.

In another aspect of the invention, there is provided a vector comprising the above-defined nucleic acid construct. Various details of the vector that could be used herein are discussed above.

In another aspect of the invention, there is provided a method for expressing a desired protein in a cell while inhibiting the expression of an undesired protein, comprising:
(a) providing a vector comprising a nucleic acid construct containing a nucleic acid molecule encoding a protein to be expressed, and a nucleic acid molecule which inhibits expression of an undesired protein as defined above, and
(b) introducing the vector in the cell.

These aspects of the present invention is particularly advantageously used in order to simultaneously suppress the expression of a protein that is not desired while expressing a protein that is desired to be expressed, in particular when an undesired protein is induced by the expression of a given protein within the same cell.

The present invention is explained in detail by reference to the following Examples, but the scope of the present invention is not limited by these Examples.

EXAMPLES

Materials and Methods

Cell Culture

The human embryonic kidney cell line HEK293 was obtained from the Riken Cell Bank (Tsukuba, Japan). The colorectal cancer cell lines DLD-1 and SW480, and the hepatocellular carcinoma cell line Hep3B were purchased from the American Type Culture Collection (Manassas, Va.). The hepatocellular carcinoma cell line HLF was from the Health Science Research Resource Bank (Osaka, Japan). HCT116 (p53−/−) cells were kindly provided by Dr. Bert Vogelstein (Johns Hopkins University). HEK293 cells were cultured in Dulbecco's Modified Eagle's medium supplemented with 10% fetal calf serum (FCS). SW480 cells were cultured in Leibovitz L-15 medium with 10% FCS. All other cell lines were cultured in RPMI-1640 medium with 10% FCS.

Plasmids

Three pre-miRNA sequences were designed that targeted the 3' untranslated region (UTR) of the human p21 mRNA using an online tool, Invitrogen's RNAi Designer (http://www.invitrogen.com). The engineered pre-miRNA sequences were designed as a mimic of the endogenous murine miR-155. The double-stranded DNA oligonucleotides corresponding to the three different p21-specific pre-miRNAs and a control sequence were individually cloned into the parental vector pcDNA6.2-GW/miR (Invitrogen) to generate pcDNA6.2-miR-p21A, pcDNA6.2-miR-p21B, pcDNA6.2-miR-p21C and pcDNA6.2-miR-control, respectively.

The three p21 pre-miRNAs were also cloned in tandem into one plasmid by multiple rounds of chaining to generate pcDNA6.2-miR-p21 which enabled co-cistronic expression of multiple miRNAs. Briefly, overhanged DNA insert is ligated to the vector provided in a cleaved state, which results in the creation of BamHI site in 5' side and BglII site in 3' side. Using the XhoI site in 3' side of BglII site, the insert digested by BamHI and XhoI is ligated in the vector by BglII and XhoI at 3' side of the DNA insert already ligated. It is possible to insert a plurality of inserts in tandem by repeating this process (see, e.g., the user manual of http://tools.invitrogen.com/content/sfs/manuals/blockit_miRNAexpressionvector_ma n.pdf, in particular the chapter 'Chaining pre-miRNAs').

An expression vector for a FLAG epitope fusion protein of p53 (pCMV-Tag2-FLAG-p53) was generated from pCMV-Tag2-FLAG (Stratagene, La Jolla, Calif.) using BamHI site at each side of the coding region of the human p53 gene. The coding region of the human p53 gene was cloned into pcDNA6.2-miR-p21 and pcDNA6.2-miR-control using SalI to generate pcDNA6.2-p53/miR-p21 and pcDNA6.2-p53/miR-control, respectively, as shown in FIG. 5. The oligonucleotide sequences of the engineered pre-miRNA and adjacent flanking regions used for plasmid construction were as follows:

TABLE 1

| | Sequence |
|---|---|
| miR-p21A (forward) | 5'-TGCTGTAGGGTGCCCTTCTTCTTGTGGTTTTGGCCACTGACTGACCACAAGAAAGGGCACCCTA-3' SEQ ID NO: 1 |
| miR-p21A (reverse) | 5'-CCTGTAGGGTGCCCTTTCTTGTGGTCAGTCAGTGGCCAAAACCACAAGAAGAAGGGCACCCTAC-3' SEQ ID NO: 2 |
| miR-p21B (forward) | 5'-TGCTGAGCTGCCTGAGGTAGAACTAGGTTTTGGCCACTGACTGACCTAGTTCTCTCAGGCAGCT-3' SEQ ID NO: 3 |
| miR-p21B (reverse) | 5'-CCTGAGCTGCCTGAGAGAACTAGGTCAGTCAGTGGCCAAAACCTAGTTCTACCTCAGGCAGCTC-3' SEQ ID NO: 4 |
| miR-p21C (forward) | 5'-TGCTGAATACTCCAAGTACACTAAGCGTTTTGGCCACTGACTGACGCTTAGTGCTTGGAGTATT-3' SEQ ID NO: 5 |
| miR-p21C (reverse) | 5'-CCTGAATACTCCAAGCACTAAGCGTCAGTCAGTGGCCAAAACGCTTAGTGTACTTGGAGTATTC-3' SEQ ID NO: 6 |

TABLE 1-continued

| | Sequence |
|---|---|
| miR-control (forward) | 5'-TGCTGAAATCGCTGATTTGTGTAGTCGTTTTGGCCACTGACTGACGACTACACATCAGCGATTT-3' SEQ ID NO: 7 |
| miR-control (reverse) | 5'-CCTGAAATCGCTGATGTGTAGTCGTCAGTCAGTGGCCAAAACGACTACACAAATCAGCGATTTC-3' SEQ ID NO: 8 |

Recombinant Adenovirus

Recombinant adenovirus was produced using the ViraPower Adenoviral Expression System (Invitrogen), according to the manufacturer's instructions. Briefly, the recombination region of each pcDNA6.2-GW/miR-based expression vector was transferred to the Gateway Vector pAd/CMV/V5-DEST using the transfer vector pDONR221 in an in vitro recombination reaction. The recombined adenoviral plasmids generated from pAd/CMV/V5-DEST in this manner were transformed into competent DH5alpha (Toyobo, Tokyo, Japan). After selection, a single clone of DH5alpha was isolated and expanded. The recombinant adenoviral plasmid was purified, and then transfected into 293A cells. After a sufficient cytopathic effect was observed in 293A cells, adenovirus was purified using the Adeno-X Virus Purification Kit (Clontech, Shiga, Japan). The recombinant adenoviruses Ad-p53/miR-21, Ad-p53/miR-control, Ad-mock/miR-p21, and Ad-mock/miR-control were generated from pcDNA6.2-p53/miR-21, pcDNA6.2-p53/miR-control, pcDNA6.2-miR-p21, and pcDNA6.2-miR-control, respectively. All insertion sequences were confirmed by nucleotide sequencing. Detailed information about the construction of recombinant adenoviruses is available from the authors upon request.

Adenovirus titer in p.f.u. was determined by plaque formation assay following infection of HEK293 cells. The multiplicity of infection (moi) was defined as the ratio of the total number of p.f.u. to the total number of cells that were infected. We titrated adenovirus from duplicate samples in order to confirm the reproducibility of the experiments.

Western Blot Analysis

The anti-p21 (Ab-1) mouse monoclonal antibody was purchased from Calbiochem (Darmstadt, Germany), anti-actin mouse monoclonal antibody was from Chemicon (Billerica, Mass.), anti-FLAG M2 mouse monoclonal antibody was from Sigma-Aldrich (St. Louis, Mo.) and anti-p53 (DO-1) mouse monoclonal antibody was from Santa Cruz Biotechnology (Santa Cruz, Calif.). Total cell lysate was extracted at 4 degree C. with RIPA buffer (150 mM NaCl, 1% NP40, 0.5% sodium deoxycholate, 0.1% SDS, 50 mM Tris HCl, pH 8.0). Samples were fractionated by SDS-PAGE and transferred onto Immobilon-P membranes (Millipore, Billerica, Mass.). Immunoreactive proteins were detected using enhanced chemiluminescence (ECL) (Amersham, Piscataway, N.J.).

Immunofluorescence Microscopy p53(−/−) HCT116 cells were grown on poly-L-lysine (PLL)-coated coverslips (Asahi Technoglass, Funabashi, Japan). After being fixed with 4% paraformaldehyde, the cells were incubated with anti-FLAG rabbit polyclonal antibody (Sigma-Aldrich) and anti-p21 mouse monoclonal antibody (Calbiochem) overnight at 4 degree C. Following incubation with Alexa Fluor 488-labeled goat anti-mouse IgG and Alexa Fluor 594-labeled goat anti-rabbit IgG (Invitrogen), the coverslips were inspected with a fluorescence microscope (Keyence, Tokyo, Japan).

Flow Cytometry

Cells ($1 \times 10^6$) were plated in 6 well plates. Twenty-four hours after plating, the cells were incubated with purified virus in 1 ml of medium supplemented with 1% FCS with brief agitation every ten minutes. For flow cytometry, at various times after infection, cells were harvested by trypsinization and pelleted by centrifugation. Pelleted cells were fixed in 90% cold ethanol, treated with RNase A (500 units/ml), and then stained with propidium iodide (50 mg/ml). Samples were analyzed on a FACSCalibur flow cytometer (BD Bioscience, San Jose, Calif.). Experiments were repeated at least three times, and 50,000 events were analyzed for each sample. Data were analyzed using FlowJo software (Tree Star, Ashland, Oreg.). For combination therapy, 24 h after infection, cells were treated with 0.5 microgram/ml of doxorubicin, and then analyzed by flow cytometry after 24 h, as described above.

RT-PCR

Total RNA was extracted from cell lines using the Trizol reagent according to instructions by the manufacturer (Invitrogen). cDNAs were obtained by reverse transcription using SuperScript Preamplification System (Invitrogen) with 2 mg of total RNA. Each PCR involved a 94 degree C., 2 min. initial denaturation step followed by 30 cycles (for miRNA, p21) and 25 cycles (for GAPDH) at 94 degree C. for 30 sec., 58 degree C. for 30 sec., and 72 degree C. for 30 sec. Oligonucleotide primer sequences were as follows:

```
miRNA:
5'-CTTGCTGAAGGCTGTATGC-3' (forward, SEQ ID NO:
10),

5'-TGGGCCATTTGTTCCATGTG-3' (reverse, SEQ ID NO:
11),

Target A-B:
5'-GGGAAGGGACACACAAGAAGAA-3' (forward, SEQ ID NO:
12),

5'-CCATCATATACCCCTAACACAGAGATAA-3' (reverse, SEQ
ID NO: 13),

Target C:
5'-CACTAACGTTGAGCCCCTGG-3' (forward, SEQ ID NO:
14),

5'-CTAGGTGGAGAAACGGGAACC-3' (reverse, SEQ ID NO:
15),

ORF:
5'-CTGGAGACTCTCAGGGTCGAA-3' (forward, SEQ ID NO:
16),

5'-GATGTAGAGCGGGCCTTTGA-3' (reverse, SEQ ID NO:
17)

GAPDH:
5' ACCACAGTCCATGCCATCAC 3' (forward, SEQ ID NO:
18),

5' TCCACCACCCTGTTGCTGTA 3' (reverse, SEQ ID NO:
19).
```

The PCR products were separated by electrophoresis on 1.5% agarose gels.

Determination of Caspase-3 Activity

Caspase-3 activity was determined by colorimetric assay using a caspase-3 assay kit (Biovision, Mountain View, Calif.), according to the manufacturer's instructions. The kit utilizes synthetic tetrapeptides labeled with p nitroanilide. Briefly, cells were lysed in the lysis buffer that was supplied with the kit. The supernatants were collected and incubated at 37 degree C. with reaction buffer containing dithiothreitol and substrates. Caspase-3 activity was determined by measuring changes in absorbance at 405 nm using a microplate reader.

Animal Models

All animals were maintained under specific pathogen free conditions and treated in accordance with guidelines set by the Animal Care and Use Committee of Sapporo Medical University. To evaluate the effect of treating established tumors, 24 female BALB/c nude mice were injected subcutaneously (s.c.) into both flanks with $2 \times 10^6$ SW480 or DLD1 cells. When the tumor size reached 100 mm³, mice received directly an intratumoral injection of $1 \times 10^9$ p.f.u. (in 100 microliter of PBS) of the indicated adenovirus a total of three times, on days 0, 1 and 2. Three mice were used for each treatment group. Tumor formation in mice was monitored for up to four weeks. The tumor volume was calculated using the equation $V \text{ (mm}^3) = a \times b2/2$, where "a" represents the largest dimension and "b" is the perpendicular diameter.

Example 1

Expression of p53 and Suppression of p21 Induction by a Single Plasmid Vector

We designed three different artificial pre-miRNA sequences (miR-p21A, B and C) that targeted the 3' untranslated region (UTR) of the p21 mRNA (FIG. 1). The pre-miRNA sequences were designed as a mimic of the endogenous murine miR-155. The structure consists of the following three parts, (i) 21-nucleotide core sequence which is completely complementary to target sites in the p21 3'UTR, (ii) 19-nucleotide sequence derived from murine miR-155 to form a terminal loop, and (iii) the sense target sequence removed two nucleotides (positions 9 and 10) to form a short internal loop which results in more efficient knockdown. The pre-miRNAs were cloned individually into a plasmid vector pcDNA6.2-GW/miR, in which expression of the engineered pre-miRNA is driven by the human cytomegalovirus (CMV) immediate early promoter.

Figure 2:
FIG. 2 shows the suppression of p21 expression by artificial miRNAs. HEK293 cells were transfected with the miRNA expression plasmids pcDNA6.2-miR-p21A, pcDNA6.2-miR-p21B and pcDNA6.2-miR-p21C, which encoded three different p21-specific artificial miRNAs (miR-p21A, B and C, respectively). Cells were also transfected with a control plasmid, pcDNA6.2-miR-control (miR-control). Total cell lysate was analyzed 24 hrs. after transfection by Western blot using anti-p21 and -actin antibodies.
Figure 3:
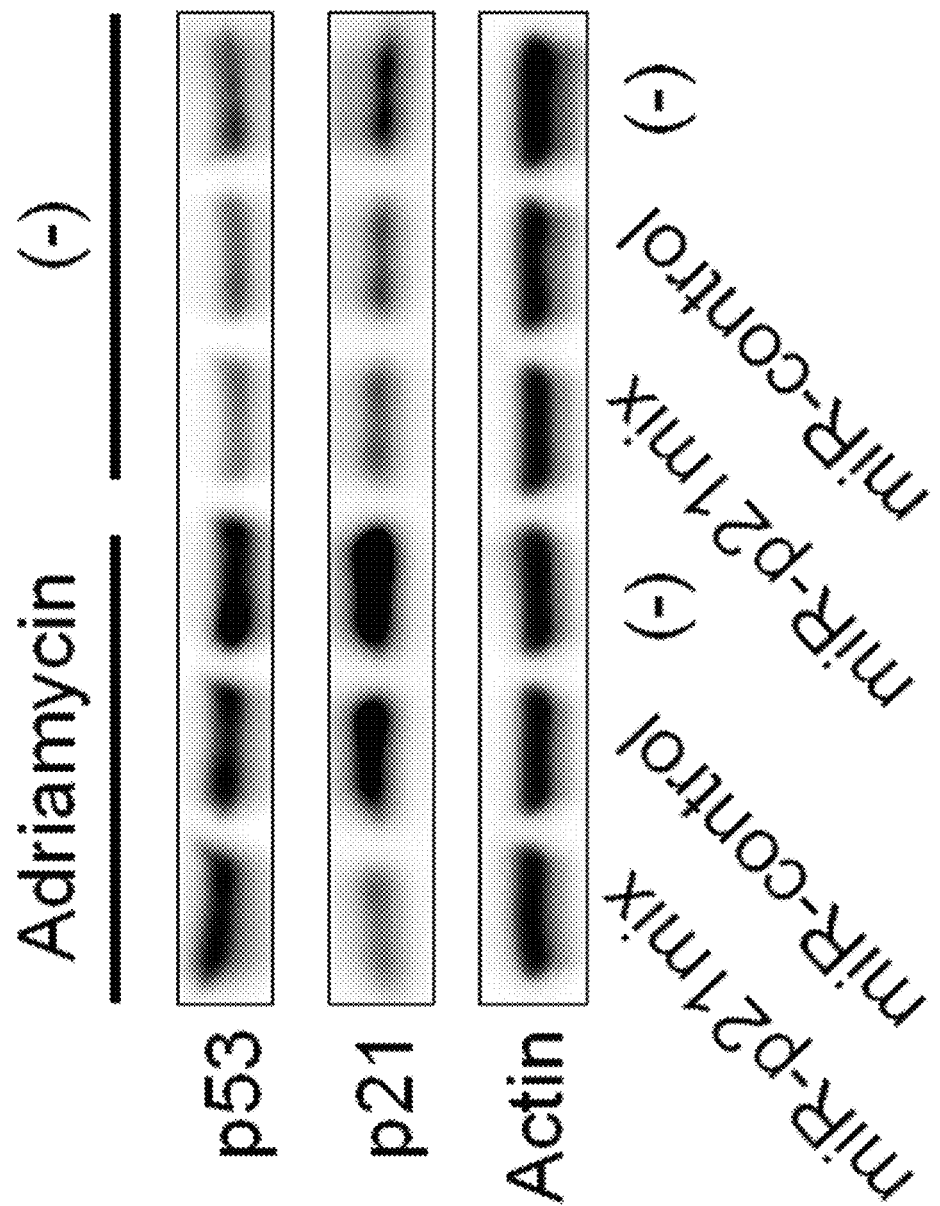
FIG. 3 shows the suppression of p21 expression by artificial miRNAs in cells treated by adriamycin (doxorubicin). HCT116 cells were transfected with a mixture of pcDNA6.2- miR-p21A, B, and C (miR-p21mix), or the control vector (miR-control). After 24 hrs., the media was replaced with fresh media with, or without, 0.5 microgram/ml of adriamycin. Total cell lysate was analyzed 24 hrs. after transfection by Western blot using anti-p53, -p21 and -actin antibodies.

In HEK293 cells, the basal level of p21 expression was suppressed by transfection using each miRNA vector individually (FIG. 2). To determine whether the induction of p21 expression following the activation of endogenous p53 was also suppressed by p21-specific miRNAs, we transfected a mixture of the three miRNA vectors into HCT116 colon cancer cells, in which wild-type p53 is activated by treatment with adriamycin. The induction of p21 gene expression in response to adriamycin was evident in cells transfected with the control miRNA vector, whereas it was suppressed in cells transfected with the mixture of p21-specific miRNA vectors (FIG. 3).

The parental miRNA plasmid used in these studies is unique in that the Pol II promoter enables co-cistronic expression of multiple miRNAs in one primary transcript, which enables the knock-down of multiple target sequences using a single vector. To determine whether the three p21-specific miRNAs functioned in a synergistic manner when expressed from a single vector, we cloned these three miRNAs in a tandem array into pcDNA6.2-GW/miR to generate pcDNA6.2-miR-p21. We then examined whether the combined expression of all three miRNAs was able to suppress the induction of p21 induced by the overexpression of exogenous p53. In HEK293 cells that overexpressed p53, the induction of p21 was suppressed by co-transfection with pcDNA6.2-miR-p21 (FIG. 4).

In co-transfection involving several vectors, all vectors may be not transfected with equal efficiency into each cell. Therefore, in some cells p53 may be overexpressed in the absence of p21 suppression, while in other cells, p21 may be suppressed in the absence of exogenous p53 expression. Several reports indicate that p21 suppression enhances cell growth through the de-repression of cell cycle arrest (van de Wetering et al., Cell 2002; 111:241-50, Gartel et al., Cancer Res 2005; 65:3980-5) and induces tumorigenesis (Van Nguyen et al., J Exp Med 2007; 204:1453-61, Poole et al., Oncogene 2004; 23:8128-34, Martin-Caballero et al., Cancer Res 2001; 61:6234-8, Barboza et al., Proc Natl Acad Sci USA 2006; 103:19842-7, Topley et al., Proc Natl Acad Sci USA 1999; 96:9089-94, Philipp et al., Oncogene 1999; 18:4689-98, Jackson et al., Cancer Res 2003; 63:3021-5). To avoid enhancing cancer cell proliferation, it may be advantageous that p21 suppression and p53 overexpression are induced simultaneously in each cell.

An unique feature of the parental miRNA vector system using Pol II promoter is that a protein coding sequence is incorporated into the vector such that the miRNA insertion site is in the 3' untranslated region (UTR) of the protein coding sequence. This feature enables co-cistronic expression of a protein of interest and an artificial miRNA that suppresses a specific target gene. We inserted the coding region of the p53 gene upstream of cluster of multiple p21-specific miRNAs, or a control miRNA sequence, to generate pcDNA6.2-p53/miR-p21 or pcDNA6.2-p53/miR-control, respectively (FIG. 5). In HEK293 cells, the transfection of pcDNA6.2-p53/miR-p21 was sufficient to express p53 and fully inhibit the induction of p21 (FIG. 6). In colon cancer cells SW480 and p53(-/-) HCT116, transfection with pcDNA6.2-p53/miR-p21 resulted in the expression of p53 and the suppression of p21 induction even in the presence of adriamycin (FIG. 7).

Example 2

Enhanced Induction of Apoptosis by a Single Adenovirus Expressing p53 and p21-Specific miRNAs In Vitro We constructed several adenoviral vectors based on the p53 and/or miR-p21 expression plasmids. To test whether the adenoviral vectors functioned in a similar manner as the plasmid vectors, we infected p53(-/-) HCT116 cells with an adenovirus that expressed p53 alone (Ad-p53/miR-control), or an adenovirus that expressed both p53 and a cluster of multiple p21-specific miRNAs (Ad-p53/miR-p21). The p53 protein level was increased following infection with Ad-p53/miR-control or Ad-p53/miR-p21 in a dose-dependent manner. Similar to the results of the transfection experiments, however, infection of cells with Ad-p53/miR-p21 resulted in the suppression of p21 induction efficiently (FIGS. 8 and 9). The expression of p53 and suppression of p21 induction was also confirmed by immunofluorescence staining (FIG. 10).

To determine the effect of adenoviral infection on apoptosis, we infected the hepatocellular carcinoma cell lines HLF (carrying mutated p53) and Hep3B (p53-null), and the colorectal carcinoma cell line DLD1 (carrying mutated p53) with adenoviruses. Western blot analysis confirmed that p53 was expressed and the induction of p21 was suppressed in these cells (FIG. 11). When we examined the cells by flow cytometry, cells that were infected with Ad-p53/miR-p21 had a significantly greater sub-G1 fraction, which is indicative of apoptotic cell death, as compared to cells infected with Ad-p53/miR-control (FIG. 12).

Not all cancer cells in which p53 is mutated are sensitive to exogenous p53 mediated apoptosis. In a previous study, we showed that SW480 colorectal cancer cells are relatively resistant to the apoptotic effect of adenovirus-mediated p53 gene transfer (Sasaki et al., Mol Cancer Ther 2008; 7:779-87). To determine whether the combined expression of p53 and p21-specific miRNAs increased the susceptibility of SW480 cells to exogenous p53-induced apoptosis, we measured the sub-G1 fraction and caspase-3 activity of cells infected with adenovirus in the presence or absence of adriamycin (FIGS. 13-15). The expression of p53 and suppression of p21 induction were confirmed by Western blot (FIG. 13). Infection of cells with Ad-p53/miR-p21 increased caspase-3 activity (FIG. 14) and the number of cells in sub-G1 (FIG. 15) as compared to cells infected with Ad-p53/miR-control.

Example 3

Therapeutic Effect of Adenovirus-Mediated Expression of p53 and p21-Specific miRNAs In Vivo To determine whether the effect of p53 expression and p21 suppression on apoptosis in vitro correlated with a therapeutic effect in vivo, we examined the activity of our novel combination adenoviral vector in a xenograft model of tumorigenesis. SW480 and DLD1 cells were injected s.c. into nude mice. When tumor volume reached a consistent size, adenovirus was injected directly into the tumor at days 0, 1 and 2 (FIG. 16, arrows). Over time, the volume of both SW480- and DLD1-derived tumors that were injected with Ad-p53/miR-p21 was less than tumors injected with Ad-p53/miR-control (FIG. 16). Note also that the injection of Ad-mock/miR-p21 resulted in an increase in tumor volume of SW480-derived tumors compared to the injection of Ad-mock/miR-control. These results indicated that p21 suppression in the absence of p53 overexpression increases the risk of tumor progression in some types of cancer, and suggested that p21 suppression should be simultaneously induced along with p53 expression in tumor cells for effective and safe cancer therapy.

[Sequence Listing]
PCT392_ST25.txt

The invention claimed is:

1. A product comprising at least one nucleic acid molecule encoding a protein of a p53 family, and at least one nucleic acid molecule which inhibits expression and/or activity of p21, wherein the product is formed as a single vector or a single nucleic acid construct.

2. A nucleic acid construct comprising: a nucleic acid molecule encoding a protein of a p53 family, and a nucleic acid molecule which inhibits expression of p21.

3. A vector comprising the nucleic acid construct of claim 2.

4. The product according to claim 1, wherein the protein of a p53 family is selected from the group consisting of p53, p63, p'73, isoform, chimera and functional fragment thereof.

5. The product according to claim 1, wherein the protein of a p53 family is p53.

6. The product according to claim 1, wherein the nucleic acid molecule which inhibits the expression of the p21 is selected from the group consisting of antisense nucleic acid, ribozyme, aptamer and RNAi effector such as miRNA, shRNA and siRNA.

7. The product according to claim 1, wherein the nucleic acid molecule which inhibits the expression of p21 is miRNA.

8. The product according to claim 1, wherein the protein of a p53 family is p53, and the nucleic acid molecule which inhibits the expression of p21 is a miRNA directed to p21.

9. The product according to claim 1, wherein the nucleic acid molecule encoding the protein of a p53 family and the nucleic acid molecule encoding the nucleic acid molecule which inhibits the expression of p21 are controlled by a same promoter.

10. The product according to claim 1, wherein the vector or the nucleic acid construct enables co-cistronic expression of the protein of a p53 family and the nucleic acid molecule which inhibits the expression of p21.

* * * * *

SEQUENCE LISTING

<160> NUMBER OF SEQ ID NOS: 28

<210> SEQ ID NO 1
<211> LENGTH: 64

```
<212> TYPE: DNA
<213> ORGANISM: Artificial sequence
<220> FEATURE:
<223> OTHER INFORMATION: miR-p21A (forward)

<400> SEQUENCE: 1
tgctgtaggg tgcccttctt cttgtggttt tggccactga ctgaccacaa gaaagggcac    60
ccta                                                                 64

<210> SEQ ID NO 2
<211> LENGTH: 64
<212> TYPE: DNA
<213> ORGANISM: Artificial sequence
<220> FEATURE:
<223> OTHER INFORMATION: miR-p21A (reverse)

<400> SEQUENCE: 2
cctgtagggt gccctttctt gtggtcagtc agtggccaaa accacaagaa gaagggcacc    60
ctac                                                                 64

<210> SEQ ID NO 3
<211> LENGTH: 64
<212> TYPE: DNA
<213> ORGANISM: Artificial sequence
<220> FEATURE:
<223> OTHER INFORMATION: miR-p21B (forward)

<400> SEQUENCE: 3
tgctgagctg cctgaggtag aactaggttt tggccactga ctgacctagt tctctcaggc    60
agct                                                                 64

<210> SEQ ID NO 4
<211> LENGTH: 64
<212> TYPE: DNA
<213> ORGANISM: Artificial sequence
<220> FEATURE:
<223> OTHER INFORMATION: miR-p21B (reverse)

<400> SEQUENCE: 4
cctgagctgc ctgagagaac taggtcagtc agtggccaaa acctagttct acctcaggca    60
gctc                                                                 64

<210> SEQ ID NO 5
<211> LENGTH: 64
<212> TYPE: DNA
<213> ORGANISM: Artificial sequence
<220> FEATURE:
<223> OTHER INFORMATION: miR-p21C (forward)

<400> SEQUENCE: 5
tgctgaatac tccaagtaca ctaagcgttt tggccactga ctgacgctta gtgcttggag    60
tatt                                                                 64

<210> SEQ ID NO 6
<211> LENGTH: 64
<212> TYPE: DNA
<213> ORGANISM: Artificial sequence
<220> FEATURE:
<223> OTHER INFORMATION: miR-p21C (reverse)

<400> SEQUENCE: 6
cctgaatact ccaagcacta agcgtcagtc agtggccaaa acgcttagtg tacttggagt    60
attc                                                                 64
```

<210> SEQ ID NO 7
<211> LENGTH: 64
<212> TYPE: DNA
<213> ORGANISM: Artificial sequence
<220> FEATURE:
<223> OTHER INFORMATION: miR-control (forward)

<400> SEQUENCE: 7

```
tgctgaaatc gctgatttgt gtagtcgttt tggccactga ctgacgacta cacatcagcg    60
attt                                                                 64
```

<210> SEQ ID NO 8
<211> LENGTH: 64
<212> TYPE: DNA
<213> ORGANISM: Artificial sequence
<220> FEATURE:
<223> OTHER INFORMATION: miR-control (reverse)

<400> SEQUENCE: 8

```
cctgaaatcg ctgatgtgta gtcgtcagtc agtggccaaa acgactacac aaatcagcga    60
tttc                                                                 64
```

<210> SEQ ID NO 9
<211> LENGTH: 2640
<212> TYPE: DNA
<213> ORGANISM: Homo Sapiens

<400> SEQUENCE: 9

```
acttgtcatg gcgactgtcc agctttgtgc caggagcctc gcaggggttg atgggattgg    60
ggttttcccc tcccatgtgc tcaagactgg cgctaaaagt tttgagcttc tcaaaagtct   120
agagccaccg tccagggagc aggtagctgc tgggctccgg ggacactttg cgttcgggct   180
gggagcgtgc tttccacgac ggtgacacgc ttccctggat tggcagccag actgccttcc   240
gggtcactgc catggaggag ccgcagtcag atcctagcgt cgagccccct ctgagtcagg   300
aaacattttc agacctatgg aaactacttc ctgaaaacaa cgttctgtcc cccttgccgt   360
cccaagcaat ggatgatttg atgctgtccc cggacgatat tgaacaatgg ttcactgaag   420
acccaggtcc agatgaagct cccagaatgc cagaggctgc tccccccgtg gcccctgcac   480
cagcagctcc tacaccggcg gcccctgcac cagcccccte ctggcccctg tcatcttctg   540
tcccttccca gaaaacctac cagggcagct acggtttccg tctgggcttc ttgcattctg   600
ggacagccaa gtctgtgact tgcacgtact cccctgccct caacaagatg ttttgccaac   660
tggccaagac ctgccctgtg cagctgtggg ttgattccac accccgccc ggcacccgcg   720 tccgcgccat ggccatctac aagcagtcac agcacatgac ggaggttgtg aggcgctgcc   780
cccaccatga gcgctgctca gatagcgatg gtctggcccc tcctcagcat cttatccgag   840
tggaaggaaa tttgcgtgtg gagtatttgg atgacagaaa cacttttcga catagtgtgg   900
tggtgcccta tgagccgcct gaggttggct ctgactgtac caccatccac tacaactaca   960
tgtgtaacag ttcctgcatg ggcggcatga accgaaggcc catcctcacc atcatcacac  1020
tggaagactc cagtggtaat ctactgggac ggaacagctt tgaggtgcgt gtttgtgcct  1080
gtcctgggag agaccggcgc acagaggaag agaatctccg caagaaaggg gagcctcacc  1140
acgagctgcc cccagggagc actaagcgag cactgcccaa caacaccagc tcctctcccc  1200
agccaaagaa gaaaccactg gatggagaat atttcaccct tcagatccgt gggcgtgagc  1260
gcttcgagat gttccgagag ctgaatgagg ccttggaact caaggatgcc caggctggga  1320
```

```
aggagccagg ggggagcagg gctcactcca gccacctgaa gtccaaaaag ggtcagtcta    1380
cctcccgcca taaaaaactc atgttcaaga cagaagggcc tgactcagac tgacattctc    1440
cacttcttgt tccccactga cagcctccca cccccatctc tccctcccct gccatttttgg   1500 gttttgggtc tttgaaccct tgcttgcaat aggtgtgcgt cagaagcacc caggacttcc    1560
atttgctttg tcccgggggct ccactgaaca agttggcctg cactggtgtt ttgttgtggg   1620
gaggaggatg gggagtagga cataccagct tagatttaa ggttttact gtgagggatg      1680 tttgggagat gtaagaaatg ttcttgcagt taagggttag tttacaatca gcccacattct   1740 aggtagggc ccacttcacc gtactaacca gggaagctgt ccctcactgt tgaattttct     1800
ctaacttcaa ggcccatatc tgtgaaatgc tggcatttgc acctacctca cagagtgcat    1860
tgtgagggtt aatgaaataa tgtacatctg gccttgaaac caccttttat tacatggggt    1920
ctagaacttg accccccttga gggtgcttgt tccctctccc tgttggtcgg tgggttggta   1980 gttttctacag ttgggcagct ggttaggtag agggagttgc caagtctctg ctggcccagc   2040
caaaccctgt ctgacaacct cttggtgaac cttagtacct aaaaggaaat ctcaccccat    2100
cccacaccct ggaggatttc atctcttgta tatgatgatc tggatccacc aagacttgtt    2160
ttatgctcag ggtcaatttc ttttttcttt ttttttttt ttttctttt tctttgagac      2220 tgggtctcgc tttgttgccc aggctggagt ggagtggcgt gatcttggct tactgcagcc    2280
tttgcctccc cggctcgagc agtcctgcct cagcctccgg agtagctggg accacaggtt    2340
catgccacca tggccagcca acttttgcat gttttgtaga gatggggtct cacagtgttg    2400
cccaggctgg tctcaaactc ctgggctcag gcgatccacc tgtctcagcc tcccagagtg    2460
ctgggattac aattgtgagc caccacgtcc agctggaagg gtcaacatct tttacattct    2520
gcaagcacat ctgcattttc accccaccct tccctcctt ctccttttt atatcccatt      2580 tttatatcga tctcttattt tacaataaaa ctttgctgcc acctgtgtgt ctgagggggtg   2640
```

<210> SEQ ID NO 10
<211> LENGTH: 19
<212> TYPE: DNA
<213> ORGANISM: Artificial sequence
<220> FEATURE:
<223> OTHER INFORMATION: Forward primer for miRNA

<400> SEQUENCE: 10
cttgctgaag gctgtatgc                                                 19

<210> SEQ ID NO 11
<211> LENGTH: 20
<212> TYPE: DNA
<213> ORGANISM: Artificial sequence
<220> FEATURE:
<223> OTHER INFORMATION: Reverse primer of miRNA

<400> SEQUENCE: 11
tgggccattt gttccatgtg                                                20

<210> SEQ ID NO 12
<211> LENGTH: 22
<212> TYPE: DNA
<213> ORGANISM: Artificial sequence
<220> FEATURE:
<223> OTHER INFORMATION: Forward primer for target A-B

<400> SEQUENCE: 12
gggaagggac acacaagaag aa                                             22

<210> SEQ ID NO 13
<211> LENGTH: 28
<212> TYPE: DNA
<213> ORGANISM: Artificial sequence
<220> FEATURE:
<223> OTHER INFORMATION: Reverse primer for target A-B

<400> SEQUENCE: 13
ccatcatata cccctaacac agagataa                                          28

<210> SEQ ID NO 14
<211> LENGTH: 20
<212> TYPE: DNA
<213> ORGANISM: Artificial sequence
<220> FEATURE:
<223> OTHER INFORMATION: Forward primer for target C

<400> SEQUENCE: 14
cactaacgtt gagcccctgg                                                   20

<210> SEQ ID NO 15
<211> LENGTH: 21
<212> TYPE: DNA
<213> ORGANISM: Artificial sequence
<220> FEATURE:
<223> OTHER INFORMATION: Reverse primer for target C

<400> SEQUENCE: 15
ctaggtggag aaacgggaac c                                                 21

<210> SEQ ID NO 16
<211> LENGTH: 21
<212> TYPE: DNA
<213> ORGANISM: Artificial sequence
<220> FEATURE:
<223> OTHER INFORMATION: Forward primer for ORF

<400> SEQUENCE: 16
ctggagactc tcagggtcga a                                                 21

<210> SEQ ID NO 17
<211> LENGTH: 20
<212> TYPE: DNA
<213> ORGANISM: Artificial sequence
<220> FEATURE:
<223> OTHER INFORMATION: Reverse primer of ORF

<400> SEQUENCE: 17
gatgtagagc gggcctttga                                                   20

<210> SEQ ID NO 18
<211> LENGTH: 20
<212> TYPE: DNA
<213> ORGANISM: Artificial sequence
<220> FEATURE:
<223> OTHER INFORMATION: Forward primer for GAPDH

<400> SEQUENCE: 18
accacagtcc atgccatcac                                                   20

<210> SEQ ID NO 19
<211> LENGTH: 20
<212> TYPE: DNA
<213> ORGANISM: Artificial sequence
<220> FEATURE:
<223> OTHER INFORMATION: Reverse primer for GAPDH

```
<400> SEQUENCE: 19
tccaccaccc tgttgctgta                                              20

<210> SEQ ID NO 20
<211> LENGTH: 69
<212> TYPE: RNA
<213> ORGANISM: Artificial sequence
<220> FEATURE:
<223> OTHER INFORMATION: miR-p21A

<400> SEQUENCE: 20
ugcuguaggg ugcccuucuu cuugugguuu uggccacuga cugaccacaa gaaagggcac   60
ccuacagga                                                          69

<210> SEQ ID NO 21
<211> LENGTH: 69
<212> TYPE: RNA
<213> ORGANISM: Artificial sequence
<220> FEATURE:
<223> OTHER INFORMATION: miR-p21B

<400> SEQUENCE: 21
ugcugagcug ccugagguag aacuagguuu uggccacuga cugaccuagu ucucucaggc   60
agcucagga                                                          69

<210> SEQ ID NO 22
<211> LENGTH: 69
<212> TYPE: RNA
<213> ORGANISM: Artificial sequence
<220> FEATURE:
<223> OTHER INFORMATION: miR-p21C

<400> SEQUENCE: 22
ugcugaauac uccaaguaca cuaagcguuu uggccacuga cugacgcuua gugcuuggag   60
uauucagga                                                          69

<210> SEQ ID NO 23
<211> LENGTH: 22
<212> TYPE: RNA
<213> ORGANISM: Artificial sequence
<220> FEATURE:
<223> OTHER INFORMATION: Part of miR-p21A corresponding to target
      sequence

<400> SEQUENCE: 23
auagggugcc cuucuucuug ug                                           22

<210> SEQ ID NO 24
<211> LENGTH: 19
<212> TYPE: RNA
<213> ORGANISM: Artificial sequence
<220> FEATURE:
<223> OTHER INFORMATION: Part of miR-p21A corresponding to target
      sequence

<400> SEQUENCE: 24
aucccacggg aaagaacac                                               19

<210> SEQ ID NO 25
<211> LENGTH: 21
<212> TYPE: RNA
<213> ORGANISM: Artificial sequence
<220> FEATURE:
<223> OTHER INFORMATION: Part of miR-p21B corresponding to target
```

-continued

```
sequence

<400> SEQUENCE: 25
agcugccuga gguagaacua g                                              21

<210> SEQ ID NO 26
<211> LENGTH: 18
<212> TYPE: RNA
<213> ORGANISM: Artificial sequence
<220> FEATURE:
<223> OTHER INFORMATION: Part of miR-p21B corresponding to target
      sequence

<400> SEQUENCE: 26
ucgacggacu cucuugau                                                  18

<210> SEQ ID NO 27
<211> LENGTH: 21
<212> TYPE: RNA
<213> ORGANISM: Artificial sequence
<220> FEATURE:
<223> OTHER INFORMATION: Part of miR-p21C corresponding to target
      sequence

<400> SEQUENCE: 27
aauacuccaa guacacuaag c                                              21

<210> SEQ ID NO 28
<211> LENGTH: 19
<212> TYPE: RNA
<213> ORGANISM: Artificial sequence
<220> FEATURE:
<223> OTHER INFORMATION: Part of miR-p21C corresponding to target
      sequence

<400> SEQUENCE: 28
uuaugagguu cgugauucg                                                 19
```